US007485446B2

(12) United States Patent
Vu et al.

(10) Patent No.: US 7,485,446 B2
(45) Date of Patent: Feb. 3, 2009

(54) STABLE RETROVIRUS AND METHODS OF USE

(75) Inventors: Halong N. Vu, Havertown, PA (US); Daniel W. Pack, Savoy, IL (US); Joshua Ramsey, Lawrence, KS (US)

(73) Assignee: The Board of Trustees of the University of Illinois, Urbanail, IL (US)

( * ) Notice: Subject to any disclaimer, the term of this patent is extended or adjusted under 35 U.S.C. 154(b) by 0 days.

(21) Appl. No.: 11/677,110

(22) Filed: Feb. 21, 2007

(65) Prior Publication Data

US 2007/0196386 A1 Aug. 23, 2007

Related U.S. Application Data

(60) Provisional application No. 60/775,233, filed on Feb. 21, 2006.

(51) Int. Cl.
*C12N 9/50* (2006.01)
*C12Q 1/70* (2006.01)
*C12N 9/00* (2006.01)
*C12N 9/48* (2006.01)

(52) U.S. Cl. ........................ 435/219; 435/183; 435/212; 435/219; 435/5; 930/10; 930/221

(58) Field of Classification Search ........................ None
See application file for complete search history.

(56) References Cited

U.S. PATENT DOCUMENTS 6,096,548 A 8/2000 Stemmer
6,596,539 B1 7/2003 Stemmer et al.
6,713,279 B1 3/2004 Short
6,846,628 B1 1/2005 Wohlstadter

OTHER PUBLICATIONS

Wlodawer, et. al. Conserved folding in retroviral proteases: crystal structure of a synthetic HIV-1 protease. Science. 1989; 245(4918):616-621.*

Masso & Vaisman. Comprehensive mutagenesis of HIV-1 protease: a computational geometry approach. Biochem Biophys Res Comm. 2003; 305:322-326.*

Kim, et al. Functional Correlates of Insertion Mutations in the Protease Gene of Human Immunodeficiency Virus Type 1 Isolates from Patients. J Virol. 2001; 75(22):11227-11233.*

Hayakawa, et al. Requirement of N- and C-terminal regions for enzymatic activitty of human T-cell leukemia virus type I protease. Eur. J. Biochem. 1992; 206:919-925.*

(Continued)

*Primary Examiner*—Mary E Mosher
*Assistant Examiner*—Stuart W Snyder
(74) *Attorney, Agent, or Firm*—Licata & Tyrrell P.C.

(57) ABSTRACT

The present invention is a mutant retroviral protease which confers an increase in retroviral stability. Retroviruses expressing the instant mutant retroviral protease exhibit at least a 2-fold increase in infectivity half-life as compared to wild-type retrovirus. Unexpectedly, a Gly119Glu mutation in the protease enhances retroviral stability in the presence of various wild-type envelope proteins including wild-type amphotropic, ecotropic and 10A1 murine leukemia viruses. The improved stability of the mutant retrovirus leads to more facile virus production and enhanced infection efficiency.

1 Claim, 4 Drawing Sheets

```
CONSENSUS  XLDDQGGXGQEXPPEPRITLKVGGQPVTFLVDTGAQHSVLTQNPGPLSDK
WT PR      ALDDQGGRGQELPPEPRITLKVGGQPVTFLVDTGAQHSVLTQNPGPLSDK
G119E-PR   ALDDQGGRGQELPPEPRITLKVGGQPVTFLVDTGAQHSVLTQNPGPLSDK
MoMLV PR   TLDDQGGQGQEPPPEPRITLKVGGQPVTFLVDTGAQHSVLTQNPGPLSDK
           *      *   *

CONSENSUS  SAWVQGATGGKRYRWTTDRKVHLATGKVTHSFLHVPDCPYPLLGRDLLTK
WT PR      SAWVQGATGGKRYRWTTDRKVHLATGKVTHSFLHVPDCPYPLLGRDLLTK
G119E-PR   SAWVQGATGGKRYRWTTDRKVHLATGKVTHSFLHVPDCPYPLLGRDLLTK
MoMLV PR   SAWVQGATGGKRYRWTTDRKVHLATGKVTHSFLHVPDCPYPLLGRDLLTK

CONSENSUS  LXAQIHFEGSGAQVXGPXGQPLQVL (SEQ ID NO:1)
WT PR      LNAQIHFEGSGAQVVGPRGQPLQVL (SEQ ID NO:2)
G119E-PR   LNAQIHFEGSGAQVVGPREQPLQVL (SEQ ID NO:3)
MoMLV PR   LKAQIHFEGSGAQVMGPMGQPLQVL (SEQ ID NO:4)
            *             *  *
```

OTHER PUBLICATIONS

Yahi, et al. Use of Drug Resistance Sequence Data for the Systematic Detection of Non-B Human Immunodeficiency Virus Type 1 (HIV-1) Subtypes: How to Creat a Sentinel Site for Monitoring the Genetic Diversity of HIV-1 at a Country Scale. J Inf Dis. 2001; 183:1311-1316.*

Fonjungo, et al. Human Immunodeficiency Virus Type 1 Group M Protease in Cameroon: Genetic Diversity and Protease Inhibitor Mutational Features. J Clin Microbiol. 2002; 40(3): 837-845.*

Nath, et al. The chimpanzee and other non-human-primate models in HIV-1 vaccine research. Trends Microbiol. 2000; 8(9):426-431.*

Cohen, J. Promising AIDS Vaccine's Failure Leaves Field Reeling. Science. 2007; 318:28-29.*

Layne, et al. Factors underlying spontaneous inactivation and susceptibility to neutralization of human immunodeficiency virus. Virology. 1992; 189(2) 695-714. Abstract Only.*

Fu, et al. Effects of Gag Mutation an Processing on Retroviral Dimeric RNA Maturation. J Virol. 2006; 80(3):1242-1249.*

Loeb, et al. Complete mutagenesis of the HIV-1 protease. Nature. 1989; 340:397-400.*

Arnold, Frances H., "Design by Directed Evolution", Acc. Chem. Res. 1998 37:125-131.

Menendez-Arias et al., "Mutational Analysis of the Substrate Binding Pocket of Murine Leukemia Virus Protease and Comparison with Human Immunodeficiency Virus Proteases", J. Biol. Chem. 1995 270(49):29162-29168.

Patnaik et al., "Genome shuffling of Lactobacillus for improved acid tolerance", Nature Biotechnology 2002 20:707-712.

Stemmer, Willem P.C., "Rapid evolution of a protein in vitro by DNA shuffling", Nature 1994 370:389-391.

Zhang et al., "Genome shuffling leads to rapid phenotypic improvement in bacteria", Natur5e 2002 415:644-646.

* cited by examiner

```
CONSENSUS  XLDDQGGXGQEXPPEPRITLKVGGQPVTFLVDTGAQHSVLTQNPGPLSDK
WT PR      ALDDQGGRGQELPPEPRITLKVGGQPVTFLVDTGAQHSVLTQNPGPLSDK
G119E-PR   ALDDQGGRGQELPPEPRITLKVGGQPVTFLVDTGAQHSVLTQNPGPLSDK
MoMLV PR   TLDDQGGQGQEPPPEPRITLKVGGQPVTFLVDTGAQHSVLTQNPGPLSDK
                *       *   *
CONSENSUS  SAWVQGATGGKRYRWTTDRKVHLATGKVTHSFLHVPDCPYPLLGRDLLTK
WT PR      SAWVQGATGGKRYRWTTDRKVHLATGKVTHSFLHVPDCPYPLLGRDLLTK
G119E-PR   SAWVQGATGGKRYRWTTDRKVHLATGKVTHSFLHVPDCPYPLLGRDLLTK
MoMLV PR   SAWVQGATGGKRYRWTTDRKVHLATGKVTHSFLHVPDCPYPLLGRDLLTK

CONSENSUS  LXAQIHFEGSGAQVXGPXGQPLQVL   (SEQ ID NO:1)
WT PR      LNAQIHFEGSGAQVVGPRGQPLQVL   (SEQ ID NO:2)
G119E-PR   LNAQIHFEGSGAQVVGPREQPLQVL   (SEQ ID NO:3)
MoMLV PR   LKAQIHFEGSGAQVMGPMGQPLQVL   (SEQ ID NO:4)
              *            *  *
```

FIG. 1

```
                                              β3
HIV-1   -----PQITLW--KRPLVTIKIG----------GQLKEAL   23
HIV-2   -----PQFSLW--KRPVVTAYIE----------GQPVEVL   23
SIV     -----PQFSLW--RRPVVTAHIE----------GQPVEVL   23
FIV     YNKVGTTTTLE--KRPEILIFVN----------GYPIKFL   28
EIAV    -----VTYNLE--KRPTTIVLIN----------DTPLNVL   23
RSV     -----LAMTMEHKDRPLVRVILTNTGSHPVKQRSVYITAL   35
MLV     --------AL--DDQGGRGQELPPEPRITLKVGGQPVTFL   30

        β3 ▽    β4       β5       β6   β7
HIV-1   LDTGADDTVIEE--MS--LPGRWKP--KM---IGGIGGFI   54
HIV-2   LDTGADDSIVAG--IE--LGNNYSP--KI---VGGIGGFI   54
SIV     LDTGADDSIVTG--IE--LGPHYTP--KI---VGGIGGFI   54
FIV     LDTGADITILNRRDFQ-VKNSIENGR-QN---MIGVGGGK   63
EIAV    LDTGADTSVLTTAHYNRLKYRGRKYQGTG---IGGVGGNV   60
RSV     LDSGADITIISEEDW--PTDWPVME--AANPQIHGIGGGI   71
MLV     VDTGAQHSVLTQNPG---------PLSDKSAWVQGATGGK   61

         β7       β8            β9  β10 β11
HIV-1   KVRQY----DQIIIEIC-------------GH-KAIGTVL   76
HIV-2   NTKEY----KNVEIEVL-------------NK-KVRATIM   76
SIV     NTKEY----KNVEIEVL-------------GK-RIRGTIM   76
FIV     RGTNY----INVHLEIRDE--------NYKTQ-CIFGNVC   90
EIAV    ETFST-----PVTIKKK-------------GR-HIKTRML   89
RSV     PMRKSRD---MIELGVINR--------DGSLERPLLLFPA  100
MLV     RYRWTTDRKVHLATGKVTHSFLHVPDCPYPLLGRDLLTKL  101

        β11     β12    α1 *  β13
HIV-1   VG---PTPVNIIGRNLLTQIGCTLNF-    99   (SEQ ID NO:5)
HIV-2   TG---DTPINIFGRNILTALGMSLNL-    99   (SEQ ID NO:6)
SIV     TG---DTPINIFGRNLLTALGMSLNF-    99   (SEQ ID NO:7)
FIV     VLEDNSLIQPLLGRDNMIKFNIRLVM-   116   (SEQ ID NO:8)
EIAV    VA---DIPVTILGRDILQDLGAKLVL-   104   (SEQ ID NO:9)
RSV     VA---MVRGSILGRDCLQGLGLRLTNL   124   (SEQ ID NO:10)
MLV     NA---QIHFEGSGAQVVGPRGQPLQVL   125   (SEQ ID NO:2)
```

FIG. 2

STABLE RETROVIRUS AND METHODS OF USE

INTRODUCTION

This application claims benefit of U.S. Provisional Patent Application Ser. No. 60/775,233, filed Feb. 21, 2006, the contents of which are incorporated herein by reference in their entirety.

BACKGROUND OF THE INVENTION

Safe and efficient gene delivery vectors are essential for the treatment of diseases (Friedmann & Roblin (1972) *Science* 175:949-955; Mulligan (1993) *Science* 260:926-932). Vector targeting, efficiency, and safety are of particular importance (Wickham (2003) *Nat. Med.* 9:135-139; Thomas, et al. (2003) *Nat. Rev. Genetics* 4:346-358; Ferber (2001) *Science* 294: 1638-1642). Viruses have evolved sophisticated mechanisms to overcome the numerous intracellular barriers encountered in gene delivery including cell entry, nuclear import, and gene expression. Viral vectors, therefore, are highly efficient and are used in the majority of ongoing gene therapy trials (Thomas & Klibanov (2003) *Appl. Microbiol. Biotechnol.* 62:27-34).

Methods have been suggested for modifying retroviruses to improve retroviral vector infection, replication, and growth.

For example, U.S. Pat. No. 6,846,628 discloses a method for identifying a nucleic acid molecule that interacts with a selection molecule to provide a replication and/or growth advantage greater than that provided a parental molecule.

U.S. Pat. No. 6,713,279 discloses a method of obtaining novel polynucleotides and encoded polypeptides by use of non-stochastic methods of directed evolution for use in evolving genetic vaccines that exhibit increased efficacy.

U.S. Pat. No. 6,596,539 teaches a method for modifying a phenotype of a virus, such as viral tropism and host range, by iterative sequence recombination of variant viruses and selection of improved variants.

U.S. Pat. No. 6,096,548 discloses a method of directing evolution of a virus to increase the efficiency with which it infects a host cell. This reference teaches directed evolution of genes involved in transfer, integration, stability or expression of the vector containing them.

Murine leukemia virus (MLV), the most commonly used retroviral vector in gene therapy clinical trials, has an infectivity half-life ($t_{1/2}$) in the range of 5 to 8 hours at 37° C. (Kotani, et al. (1994) *Hum. Gene Ther.* 5:19-28; Andreadis, et al. (1997) *J. Virol.* 71:7541-7548; Le Doux, et al. (1999) *Biotechnol. Bioeng.* 63:654-662; Merten (2004) *J. Gene Med.* 6:S105-S124). This instability limits both virus production and the maximum achievable virus titer as the decay of active virus particles competes with the rate of their generation by producer cells (Merten, et al. (2004) supra; Le Doux, et al. (1999) *Biotechnol. Bioeng.* 63:654-662). The instability also limits gene transfer efficiency, increasing the dose of virus required to transduce a given number of target cells, thereby increasing costs and raising safety concerns. A more stable retrovirus vector is needed to improve transduction efficiency and virus production, leading to important practical implications. The present invention meets this need in the art.

Should include references teaching the envelope protein as source of instability? I see that this is mentioned in the examples, so maybe not necessary to include here.

SUMMARY OF THE INVENTION

The present invention is a mutant retroviral protease having an amino acid substitution at position 119 of SEQ ID NO:1, or a structural and functional homolog thereof, wherein said mutant retroviral protease increases the stability of a retrovirus. Particular embodiments embrace a stable mutant virus expressing the mutant retroviral protease of the present invention.

The present invention is also a method for generating a stable mutant retrovirus. The method involves generating a mutant library of a parental retrovirus and selecting for a stable mutant virus having a mutant protease. A stable mutant virus generated by this method is also provided.

The present invention also embraces a method for increasing viral production, titer and infection efficiency of a retrovirus. The method involves expressing, from a retroviral nucleic acid molecule, a mutant retroviral protease of the present invention thereby increasing viral production, titer and infection efficiency of the retrovirus.

BRIEF DESCRIPTION OF THE DRAWINGS

FIG. 1 shows a consensus sequence (SEQ ID NO:1) of 4070A wild-type protease (wt-PR; SEQ ID NO:2) and wild-type Moloney ecotropic protease (MoMLV PR; SEQ ID NO:3) and amino acid sequence alignment with Gly119Glu protease (G119E-PR; SEQ ID NO:4). The Gly119Glu mutation is in bold, and differences between 4070A and MoMLV proteases are indicated by an asterisk.

FIG. 2 is an amino acid sequence alignment of retroviral proteases (PRs) based on the solved three-dimensional structures of HIV-1 (human immunodeficiency virus type 1), HIV-2 (human immunodeficiency virus type 2), SIV (simian immunodeficiency virus), FIV (feline immunodeficiency virus), EIAV (equine infectious anemia virus), and RSV (Rous sarcoma virus) PRs. See Wlodawer and Gustchina (2000) *Biochim. Biophys. Acta* 1477:16-34. The MLV PR sequence was aligned by sequence similarity. Identical residues are bold and underlined, and conserved residues are in bold. The location of the Gly119 residue in the MLV PR is indicated by an asterisk. Secondary structure elements from RSV sequence are represented over the alignment. βBeta strand elements; α, alpha helix. The triangle indicates that location of the active site. See also Marmey, et al. (2005) *J. Virol.* 2:33.

DETAILED DESCRIPTION OF THE INVENTION

Figure 3:
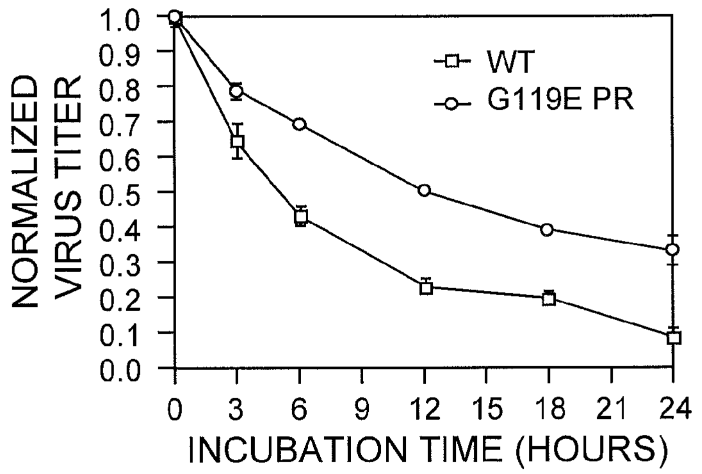
FIG. 3 shows the decay of wild-type (wt) and Gly119Glu-PR MLV infectivity (n=3; error bars represent standard deviation). The wild-type half-life was 6.8 hours ($r^2$=0.958), while that of Gly119Glu-PR MLV was 13.9 hours ($r^2$=0.967).

Directed evolution is an effective method for generating novel or desired properties of proteins (Stemmer (1994) *Nature* 370:389-391; Arnold (1998) *Acc. Chem. Res.* 31:125-131) and genomes (Zhang, et al. (2002) *Nature* 415:644-646; Patnaik, et al. (2002) *Nat. Biotechnol.* 20:707-712). It has now been found that directed evolution is also useful for generating a retrovirus with a half-life approximately four times the infectivity half-life of wild-type retrovirus. By way of illustration, the amphotropic MLV genome (including gag, pro, pol and env) with a half-life of ~6.8 hours was randomly mutated and infectious particles were selected for after prolonged incubation at 37° C. With a single round of mutagenesis and several rounds of selection, a variant MLV population with $t_{1/2}$=~12 hours at 37° C. was generated. Isolation of individual, improved mutants unexpectedly revealed that a single mutation in the viral protease, Gly119Glu, was responsible for the enhanced phenotype, even in the presence of wild-type (4070A strain) envelope protein, a protein generally believed in the art to impart viral instability. The proteases of wild-type 4070A and wild-type Moloney ecotropic share significant sequence identity (FIG. 1), and the stability of Moloney (ecotropic), as well as 10A1, was also improved by the Gly119Glu mutation. Moreover, substituting other amino acids, via saturation mutagenesis, at position 119 of the viral protease resulted in even longer mutant MLV half-lives (e.g. Gly119Pro-PR, $t_{1/2}$=~24 hours), approaching four times that of wild-type MLV. These data indicate that the inherent instability of retrovirus particles is not imposed by an instability of the virus envelope protein; rather, the viral protease is a source of retroviral instability leading to the limited half-life of retroviruses at physiological conditions. Accordingly, the present invention relates to mutant retroviral proteases for use in generating stable and efficient gene delivery retroviral vectors.

As used in the context of the present invention, a retrovirus is intended to include any member of the family Retroviridae, in particular of the genera Alpharetrovirus including Avian leukosis virus, Avian sarcoma virus CT10, and Rous sarcoma virus; Betaretrovirus including Jaagsiekte sheep retrovirus, Mason-Pfizer monkey virus, and Mouse mammary tumor virus; Deltaretrovirus including Bovine leukemia virus and Primate T-lymphotropic viruses; Epsilonretrovirus including Snakehead retrovirus and Walleye dermal sarcoma virus; Gammaretrovirus including the Avian (Reticuloendotheliosis) virus group (e.g., Spleen necrosis virus) and Mammalian virus group (e.g., feline leukemia virus, murine leukemia virus, Moloney murine sarcoma virus, and Simian sarcoma virus); and Lentivirus including Bovine lentivirus group (e.g., bovine immunodeficiency virus), Equine lentivirus group (e.g., Equine infectious anemia virus), Feline lentivirus group (e.g., Feline immunodeficiency virus), and Primate lentivirus group (e.g., Human immunodeficiency virus 1, Human immunodeficiency virus 2, and Simian immunodeficiency virus).

Retroviruses are enveloped viruses containing a genome composed of two copies of a single-stranded RNA molecule. Following infection, the retroviral genome is reverse-transcribed into double-stranded DNA, which integrates into the host genome. The viral genome is approximately 10 kb and is composed of at least gag, pro, pol, and env loci (Coffin (1996) In: *Fundamental Virology*, Fields, et al., Editors. Lippincott-Raven, Philadelphia, Pa.). The gag coding region produces the matrix, capsid, and nucleocapsid structural proteins, whereas pro and pol encode the protease (PR), reverse transcriptase, and integrase enzymes. Further, env encodes the Env glycoprotein generally composed of two subunits, SU and TM, which bind the target-cell receptor and mediate virus-cell membrane fusion, respectively. The observed instability of MLV has been attributed to a labile SU-TM interaction that allows the SU subunit to be shed from the envelope spontaneously or in response to physical forces (Pinter, et al. (1978) *Virology* 91:345-351; Yee, et al. (1999) *Proc. Natl. Acad. Sci. USA* 91:9564-9568; Powell, et al. (2000) *Nat. Biotechnol.* 18:1279-1282). At each end of the genome are long terminal repeats (LTRs) which include promoter/enhancer regions and sequences involved with integration. In addition there are sequences required for packaging the viral DNA (psi) and RNA splice sites in the env gene.

A retrovirus of the present invention is intended to specifically encompass retroviral vectors for packaging and delivering heterologous DNA to dividing or non-dividing cells. Generally, there are two types of vectors: replication competent (see, e.g., U.S. Pat. No. 6,492,166) and replication incompetent. A common strategy in the production of replication incompetent retroviral vectors employs the use of packaging viruses or cell lines (also known as helper cells) to package heterologous RNA molecules. These RNA molecules have limited retroviral sequences (e.g., LTR and viral integrase sequences) and commonly express a messenger RNA of interest (e.g., vector encoding a heterologous protein), and in some cases a selectable marker such as a drug-resistance gene. To prevent recombination resulting in replication competent retroviruses, regions of homology with the vector sequence are removed and the non-essential genes are expressed by at least two transcriptional constructs (Markowitz, et al. (1988) *J. Virol.* 62:1120-1124). One construct contains the gag/pol region, and the second construct contains the env gene. The viral RNA encoding these functions is not packaged into virus particles because the RNA sequences needed for binding to Gag proteins (i.e., the packaging signal, or Ψ) are generally deleted from the retroviral genome constructs. In contrast, the vector sequence encoding the heterologous protein contains the packaging signal and is therefore packaged into virus particles.

Virus particles are harvested from packaging cell lines transfected with the vector sequence, and these particles are used to transduce the vector sequence (as well as the limited retroviral sequences) into target cells bearing the appropriate receptors for the retroviral or other viral envelope proteins expressed on the virus particles. Because the retrovirus genome is not intact in the packaging cell lines, these viruses are generally referred to as replication incompetent. Once the vector sequence enters the target cell, it is reverse-transcribed into DNA, and the two retroviral LTR and the viral integrase mediate integration of the vector sequence into the target cell DNA. As will be appreciated by one of skill in the art, the mutant retroviral protease of the present invention can be used in combination with any type of retroviral vector including both replication incompetent vectors and replication competent retroviral vectors with the effect of increasing the infectivity half life, viral production and infection efficiency of the retroviral vector.

Retroviral proteases have conserved functional activity and structural features (FIG. 2). Retroviruses in general, and Lentiviruses in particular with half-lives of 4 to 9 hours at 37° C. (Zhang, et al. (2004) *Genet. Vacc. Ther.* 2:6; Layne, et al. (1992) *J. Virol.* 189:695-714), are useful gene therapy vectors. Accordingly, an increase in stability, viral production, titer and infection efficiency of retroviral vectors facilitates the use of retroviruses in the delivery of genes in vivo. Accordingly, mutations disclosed herein which increase the stability of MLV, 10A1 MLV and MoMLV are mutations which can be used to increase the stability of other retroviruses. Thus, the present invention is a mutant retroviral protease selected for its ability to increase the stability of a retrovirus. The instant protease is a mutant in the sense that the amino acid sequence of the protease contains one or more amino acids not present in the wild-type amino acid sequence. Specifically, the present invention embraces the mutation of a retroviral protease of SEQ ID NO:1, or structural and functional homologs thereof (e.g., as depicted in FIG. 2). In one embodiment, the mutation is an amino acid substitution. In another embodiment, the mutation is located at amino acid position 119 of SEQ ID NO:1, or an amino acid at the same structural position in a functional or structural homolog of SEQ ID NO:1.

To mutate a retroviral protease amino acid sequence specifically disclosed herein or otherwise known in the art, amino acid substitutions based on any characteristic known in the art can be made, including the relative similarity or differences of the amino acid side-chain substituents, for example, their hydrophobicity, hydrophilicity, charge, size, and the like. In particular embodiments, an amino acid substitution at amino acid position 119 of SEQ ID NO:1 is one which modulates the electrostatic interactions or steric effects in the antiparallel β-sheet of the protease dimer. As exemplified herein, replacing the nonpolar Gly119 with a charged amino acid residue such as Glu, Arg, Lys, or Asp, significantly increased retroviral infectivity half-life.

Mutation of SEQ ID NO:1, or functional and structural homologs thereof, is achieved by site-specific mutagenesis or any other art-established method for generating a mutation at a particular amino acid residue. Alternatively, a retroviral protease which increases the stability of a retrovirus can be identified from a random library of mutants. Such libraries can be generated by any method known in the art. However, particular embodiments embrace the generation of the mutants by directed evolution. By "directed evolution" is meant the generation and selection or screening of a pool of mutated nucleic acid molecules having sufficient diversity for a nucleic acid molecule encoding a mutant retroviral protease which confers retroviral stability to be present. The template nucleic acid for the mutant library is generally a nucleic acid molecule encoding a wild-type protease or pol gene or a parental retrovirus genome. The template can be used in any of the amplification techniques described herein to generate a library of mutant proteins or genomes. The library of mutant proteins or genomes is screened based on an increase in stability, infectivity half-life, viral production, titer, and/or infection efficiency. The screens can be reiterated until the desired retroviral stability is obtained or, alternatively, a nucleic acid molecule encoding a mutant protease can be used as a template to generate one or more secondary libraries of mutant proteins to screen for the same or different phenotype.

The mutant library can be generated using any method known in the art. As exemplified herein, a mutant library can be generated in vivo with a bacterial mutator strain. Alternatively, the library can be made by any one of the well-established in vitro PCR amplification techniques including, but not limited to, error-prone PCR (U.S. Pat. Nos. 5,605,793; 5,811,238; 5,830,721); assembly PCR (U.S. Pat. No. 6,806, 048); DNA shuffling (WO 00/42561 and WO 01/70947); multiple amplification reactions with pooled oligonucleotides (U.S. Pat. No. 6,403,312); exon shuffling (U.S. Pat. No. 6,365,377; Kolkman & Stemmer (2001) *Nature Biotechnology* 19:423-428); family shuffling (Crameri, et al. (1998) *Nature* 391:288-291; U.S. Pat. No. 6,376,246); RACHITT™ (Coco, et al. (2001) *Nature Biotechnology* 19:354-359; WO 02/06469); STEP and random priming of in vitro recombination (Zhao, et al. (1998) *Nature Biotechnology* 16:258-261; Shao, et al. (1998) *Nucl. Acids Res.* 26:681-683); exonucleases-mediated gene assembly (U.S. Pat. Nos. 6,352,842 and 6,361,974); GENE SITE SATURATION MUTAGENESIS™ (U.S. Pat. No. 6,358,709); GENE REASSEMBLY™ (U.S. Pat. No. 6,358,709) and SCRATCHY (Lutz, et al. (2001) *Proc. Natl. Acad. Sci. USA* 98:11248-11253); DNA fragmentation methods (Kikuchi, et al. (1999) *Gene* 236:159-167); and single-stranded DNA shuffling (Kikuchi, et al. (2000) *Gene* 243:133-137).

Although the above disclosed methods are intended to introduce random mutations throughout a gene or genome, those skilled in the art will appreciate that specific regions of a gene or genome can be mutated, and others left untouched, either by isolating and combining the mutated region with the unmodified region, e.g., by cassette mutagenesis (see, WO 01/75767; Kim & Mass (2000) *Biotechniques* 28:196-198; Lanio & Jeltsch (1998) *Biotechniques* 25:958-965; Ge & Rudolph (1997) *Biotechniques* 22:28-30; Ho, et al. (1989) *Gene* 77:51059).

A number of other methods can also be used to generate the libraries disclosed herein. For example, in some embodiments, oligonucleotide-directed mutagenesis can be used. Oligonucleotide-directed mutagenesis refers to a process that allows for the generation of site-specific mutations in any cloned DNA segment of interest. See, e.g., Ehrlich (1989) *PCR Technology*, Stockton Press; Oliphant, et al. (1986) *Gene* 44:177-183; Reidhaar-Olson, et al. (1988) *Science* 241: 53-57; Hermes, et al. (1990) *Proc. Natl. Acad. Sci. USA* 87:696-700; Knowles (1987) *Science* 236:1252-258. As another specific example, classical site-directed mutagenesis, e.g. QUICKCHANGE™ commercially available from STRATAGENE® can be used to generate the libraries described herein. As another example, cassette mutagenesis can be used. In some embodiments, cassette mutagenesis includes the creation of DNA molecules from restriction digestion fragments using nucleic acid ligation, and the random ligation of restriction fragments (Kikuchi, et al., (1999) supra). Additionally, cassette mutagenesis can be performed using randomly-cleaved nucleic acids (Kikuchi et al. (2000) supra), by PCR-ligation PCR mutagenesis (see, for example, Ali & Steinkasserer (1995) *Biotechniques* 18:746-750), by seamless gene engineering using RNA- and DNA-overhang cloning (Coljee, et al. (2000) *Nature Biotechnology* 18:789-791), by ligation-mediated gene construction, or by homologous or non-homologous random recombination (U.S. Pat. Nos. 6,368,861; 6,423,542; 6,376,246; 6,368,861; 6,319,714; and WO 00/42561; WO 00/42561; WO 00/42560; WO 00/42560; WO 00/42559; WO 00/18906; WO 00/18906; and WO 00/18906).

In addition to the PCR methods outlined herein, other amplification and gene synthesis methods can be used to generate the instant libraries. For example, the library can be "stitched" together using pools of oligonucleotides with polymerases (and optionally or solely) ligases. These resulting variable sequences can then be amplified using any number of amplification techniques, including, but not limited to, polymerase chain reaction (PCR), strand displacement amplification (SDA), nucleic acid sequence-based amplification (NASBA), ligation chain reaction (LCR) and transcription-mediated amplification (TMA). In addition, there are a number of variations of PCR which can also find use in the invention, including quantitative competitive PCR (QC-PCR), arbitrarily-primed PCR (AP-PCR), immuno-PCR, Alu-PCR, PCR single-strand conformational polymorphism (PCR-SSCP), reverse transcriptase PCR (RT-PCR), biotin-capture PCR, vectorette PCR, panhandle PCR, and PCR-select cDNA subtraction, among others. Furthermore, by incorporating the T7 polymerase initiator into one or more oligonucleotides, IVT amplification can be performed.

Libraries of mutants can subsequently be amplified and screened for the desired phenotype. As exemplified herein, a mutant retroviral library was generated in an XL1-Red strain, subjected to reiterative 37° C. incubations and selected for the ability to infect mammalian cells. Desirably, the mutant retroviral protease is selected based upon its ability to increase the stability, or more particularly the thermostability, of a retrovirus. In accordance with the teachings herein, an increase in the stability or thermostability of a retrovirus expressing the mutant retroviral protease refers to an increase in the infectivity half-life of the retrovirus under physiological conditions (i.e., at or near 37°) as compared to a wild-type retrovirus. Infectivity half-life refers to virus titer plotted against the incubation time to estimate the point at which 50% of the viral infectivity is lost. In some embodiments, the infectivity half-life of a retrovirus expressing the mutant protease is at least 2-fold the infectivity half-life of a wild-type virus. In other embodiments, the infectivity half-life of a retrovirus expressing the mutant protease is at least 4-fold the infectivity half-life of a wild-type virus.

In addition to a mutation at position 119 of SEQ ID NO:1, a library screen of the present invention will also identify other mutant proteases that generate a stable mutant retrovirus. Exemplary mutant proteases identified by the screening method of the invention include, for example, mutations at Glu15 (e.g., Glu15Arg), His37 (e.g., His37Asp), Val39 (e.g., Val39Ile), and Ala57 (e.g., Ala57Ile).

Advantageously, by increasing the stability or infectivity half-life of a retrovirus, the instant mutant retroviral protease also increases viral production and infection efficiency of a retrovirus. Accordingly, the instant invention embraces expressing, from a retroviral nucleic acid, a mutant retroviral protease of the present invention to increase viral production (i.e., the total active virus output over the duration of the virus collection period) by a host cell, titer (i.e., a measure of the number of active virus particles per unit volume) and viral infection efficiency (i.e., the number of infected cells as compared to non-infected cells) as compared to a wild-type retrovirus.

Retroviruses and retroviral vectors of the present invention find application in the delivery of heterologous nucleic acid molecules to a target cell. A heterologous nucleic acid molecule or transgene generally refers to a sequence that does not normally exist in the wild or a sequence that originates from a foreign species or, if from the same species, it may be substantially modified from its original form. Alternatively, an unchanged nucleic acid molecule that is not normally expressed in a cell is a heterologous nucleic acid molecule.

Depending upon the intended use of the retroviral vector of the present invention, any number of heterologous nucleic acid molecules can be inserted into the retroviral vector. For example, for in vitro studies, commonly used marker genes or reporter genes can be used, including, antibiotic resistance and fluorescent molecules (e.g., GFP). Additional nucleic acid molecules encoding any desired polypeptide can also be inserted into the retrovirus or retroviral vector of the present invention. Where in vivo delivery of a heterologous nucleic acid molecule is sought both therapeutic and non-therapeutic molecules can be used. For example, the heterologous nucleic acid molecule can encode a therapeutic molecule including antisense molecules or ribozymes directed to a particular gene associated with a cell proliferative disorder, the heterologous molecule can be a suicide gene (e.g., HSV-tk or PNP), or a therapeutic protein (e.g., Factor IX).

Other therapeutic proteins applicable to the present invention are readily identified in the art (see for example, Crystal (1995) *Science* 270:404-410). In addition, numerous gene therapy methods that take advantage of retroviral vectors for treating a wide variety of diseases are well-known in the art (see, e.g., U.S. Pat. Nos. 4,405,712 and 4,650,764; Friedmann (1989) *Science* 244:1275-1281; Mulligan (1993) *Science* 260:926-932). An increasing number of these methods are currently being applied in human clinical trials (Morgan (1993) *BioPharm.* 6(1):32-35; and *The Development of Human Gene Therapy*, Theodore Friedmann, Ed., Cold Spring Harbor Laboratory Press, Cold Spring Harbor, N.Y., 1999). The safety of these currently available gene therapy protocols can be substantially increased by using retroviral vectors of the present invention. For example, given the increased infectivity half-life, viral production and infection efficiency, the instant retroviruses provide a decrease in the required vector dose, thereby lessening vector exposure and administrations for the gene therapy treatment.

The invention is described in greater detail by the following non-limiting examples.

EXAMPLE 1

Materials and Methods

Cell lines. HEK-293, HEK-293T, and NIH 3T3 cells were obtained from American Type Culture Collection (ATCC, Manassas, Va.). GP-293 Luc packaging cells stably express the Moloney murine leukemia virus (MoMLV) gag-pol gene products as well as a luciferase-encoding viral RNA transcript (BD BIOSCIENCES CLONTECH™, Mountain View, Calif.). All cell lines were maintained in Dulbecco's modified Eagle's medium (DMEM) with 10% fetal bovine serum (FBS), except NIH 3T3, which were grown in DMEM with 10% calf serum.

Plasmids. pA14 encodes an infectious amphotropic clone of MLV, containing the MLV genome in a permutated form at the SalI site in the pol gene. pMD.M EcoEnv expresses the ecotropic MoMLV envelope protein driven by a CMV promoter. The ecotropic envelope sequence of pMD.M EcoEnv was replaced, between sites SacII and ClaI, by the 4070A env gene from pMo(4070A)(Han, et al. (1998) *J. Virol.* 72:9101-9108) to produce pMD.M(4070A). The 10A1 env of pMo (10A1)(Han, et al. (1998) supra) was cloned into the pLXRN (CLONTECH™) between Sal1 and AvrII sites to produce pL(10A1)RN. pVSV-G (CLONTECH™) expresses the envelope glycoprotein of the vesicular stomatitis virus (VSV). Retroviral vectors pLZCX2 and PLLRN (CLONTECH™) contain the lacZ and luciferase reporter genes, respectively. The neomycin resistance gene of pLNCX2 (CLONTECH™) was replaced with lacZ from pSV-β-Gal (PROMEGA®, Madison, Wis.) to yield pLZCX2. pLNCX2 was digested with EcoRI and re-ligated to remove the 5'LTR and Ψ packaging signal, forming pNCX2. The gag-pol sequence from pA14 was cloned into pNCX2 from sites NotI and StuI to yield pNCgag-pol. Further, pCMVgag-pol encodes the MoMLV gag-pol genes under control of the cytomegalovirus promoter (Burns, et al. (1993) *Proc. Natl. Acad. Sci. USA* 90:8033-80370).

Mutagenesis, Library Expression, and Selection. The variant virus library was generated by transforming 50 ng pA14 into the XL1-Red bacteria mutator strain (STRATAGENE®, La Jolla, Calif.) according to the manufacturer's instructions. The cells were passaged in Luria broth (LB) media for 3 days at 37° C., diluting the culture 1:1000 after each day. Parental or mutagenized pA14 DNA was recovered by QUANTUM PREP® maxiprep (BIO-RAD®, Hercules, Calif.) and transfected into HEK-293 cells with LIPOFECTAMINE™ 2000 (INVITROGEN™, Carlsbad, Calif.). Namely, $3\times10^6$ HEK-293 cells, in a 60-mm plate, were transfected with 10 μg DNA. At 48 hours post-transfection, "primary" virus-containing supernatant (4 ml) was collected, filtered (0.45-μm cellulose acetate, CORNING® Inc., Corning, N.Y.), and 2 mL used to infect naïve HEK-293 cells for "secondary" virus propagation. Medium was replaced every 24 hours, and 4 days post-transfection the secondary virus supernatant was collected, filtered, incubated for 12 hours at 37° C., and used to infect naïve HEK-293 cells. This cycle of virus propagation, extended 37° C. incubation, and infection of HEK-293 cells was repeated for seven rounds. The population of XL1-Red cells in culture was greater than $10^{11}$ clones when counted by limiting dilution. With transfection efficiencies of 50-80% for HEK-293 cells and $3\times10^6$ cells at transfection, the effective size of the library was $>10^6$ variant viruses. Viruses produced from the mutated pA14 library exhibited ~50% of the titer of viruses produced using the wild-type vector, which was deemed to represent a reasonable compromise between possible functional and inactivated mutants.

Isolation of Mutants and Screening. To isolate individual virus clones from the variant virus population remaining after the selection process, viral RNA was purified directly from the supernatant with the NUCLEOSPIN® RNA virus kit (Macherey-Nagel, Düren, Germany). Viral env or gag-pol sequences were subsequently recovered by RT-PCR and cloned into pNCX2, between NotI and StuI sites. Primer sequences were as follows: env5661f, 5'-ATT GCG GCC GCT TAC ACA GTC CTG CTG ACC AC-3' (SEQ ID NO:11); env7851rev, 5'-CCG ATA TCT CCA TGC CTT GCA AAA TGG CGT TAC TTA AG-3' (SEQ ID NO:12); gp73f, 5'-TAG CGG CCG CAC TTG TGG TCT CGC TGT TCC-3' (SEQ ID NO:13); gp6050rev, 5'-CGA CAT ACG GTT CCT GGT CT-3' (SEQ ID NO:14). Cloned sequences were tested by transfection into GP-293 Luc cells (envelope mutants), or HEK-293T cells (gag-pol mutants). Improved stability and infection were screened by comparing virus transduction before and after a 24-hour incubation at 37° C.

Site-directed Mutagenesis. Site-directed mutagenesis of pNCgag-pol and pCMVgag-pol were performed with the QUIKCHANGE® XL mutagenesis kit (STRATAGENE®, La Jolla, Calif.) using the following primer and reverse complement pairs, gp-qc1952forw, 5'-GGT TGT GGG ACC AAG GGA ACA GCC CCT GCA AGT GC-3' (SEQ ID NO:15); gp-qc1952rev, 5'-GCA CTT GCA GGG GCT GTT CCC TTG GTC CCA CAA CC-3' (SEQ ID NO:16); CMV-qc1952forw, 5'-GGT TAT GGG ACC AAT GGA GCA GCC CCT GCA AGT GT-3' (SEQ ID NO:17); GC-CMV-qcl952forw, 5'-ACA CTT GCA GGG GCT GCT CCA TTG GTC CCA TAA CC-3' (SEQ ID NO:18).

Virus Production and Titer. Generally, $1\times10^6$ HEK-293T cells were transfected with 2 μg each of pMDM(4070A), pNCgag-pol, and pLLRN or pLZCX2, with 20 pL LIPOFECTAMINE™ 2000. At 48 hours and 72 hours post-transfection, virus-containing supernatant was harvested from the cells, filtered (0.45 μm), aliquoted, and used immediately or stored at −80° C. pMDM.EcoEnv, pL(10A1)RN, or pVSV-G was transfected in place of pMDM (4070A) for production of ecotropic, 10A1, and VSV-G pseudotyped viruses, respectively. To determine virus titer, ten-fold serial dilutions of lacZ-encoding virus supernatant containing 8 μg/mL POLYBRENE® (Specialty Media, Phillipsburg, N.J.) were used to infect $5\times10^5$ HEK-293 cells in six-well plates for 6 hours (or as indicated). After 2 days, target cells were fixed with formaldehyde and glutaraldehyde (2% and 0.2% vol/vol, respectively) and stained with X-gal (STRATAGENE®), and infected cells were counted microscopically. For viruses generated by pA14 without a selection marker, virus titer was monitored by marker rescue with GP2-293 Luc cells, which stably express the luciferase reporter vector pLLRN. Supernatant of pA14 viruses passaged on GP2-293 Luc cells was used to infect HEK-293 cells, and Ψ-luc virus titer was measured as luciferase activity assay (PROMEGA®).

Retrovirus Decay. Frozen wild-type and mutant virus stocks from transfection were thawed in a 37° C. water bath and aliquoted. The 0 hour sample was refrozen at −80° C., and the remaining virus samples were incubated at 37° C. or 4° C., 5% $CO_2$ for the times indicated and then frozen at −80° C. Viruses were later thawed and tittered by measuring transduction of luciferase in HEK-293 cells by the luciferase assay (PROMEGA®). Typically, viruses were diluted 5- to 10-fold so that infections were performed at low multiplicity of infection (MOI<1) to more accurately measure virus transduction as a function of active virus concentration (Le Doux, et al. (1999) supra).

Freeze/thaw and Ultracentrifugation. For freeze/thaw experiments, wild-type and thermostable mutant virus supernatants were collected from transfected HEK-293T cells, filtered, and aliquoted. The 0 time point was refrigerated at 4° C. and the remaining samples subjected to freezing (−80° C.) and thawing (37° C. water bath). For ultracentrifugation, virus samples were aliquoted and diluted to 10 mL and spun at 120,000×g for 1 hour at 4° C. in an SW-28 Beckman rotor and L-8 ultracentrifuge (Beckman Coulter, Fullerton, Calif.). Samples were removed and placed at 4° C. overnight for resuspension. All viruses were warmed to 37° C. prior to infection.

Virus Transduction. Virus stocks containing the luc reporter were diluted in DMEM with 10% FBS, and POLYBRENE® was added to a concentration of 8 μg/mL. Subsequently, 2 mL virus was added to 5×10$^5$ HEK-293 target cells in six-well plates. Virus infection times were 30 minutes, 24 hours, and 48 hours, with the virus supernatant replaced after 24 hours during the 48-hour infection period. Virus transduction was measured the following day after virus infection with the luciferase activity assay. The brief 30 minute infection obtains an initial titer that minimizes the effect of virus decay for both the wild-type and mutant virus samples. This initial measurement was used as a normalization factor. Infections were performed at low multiplicity of infection (MOI<1) to more accurately measure virus transduction as a function of active virus concentration (Le Doux, et al. (1999) supra).

Site-Saturation Mutagenesis and Screening. Substitution of amino acids at position 119 of the MLV PR in pNCgag-pol was carried out with the QUIKCHANGE® XL mutagenesis kit (STRATAGENE®, La Jolla, Calif.) using the following primers listed in Table 1, with their reverse complements (not shown).

To revert the Gly119Pro-PR mutant back to wild-type, primer qc1952 wt-f, 5'-GGT TGT GGGACC AAG GGG ACA GCC CCT GCA AGT GC-3' (SEQ ID NO:37) was employed. All clones were sequenced to verify codon changes prior to transfection and screening.

Primers for Glu15Arg, His36Asp, Val39Ile, and Ala57Ile PR mutants were qc-e15arg, 5'-TCA GGA GCT CCC CCC T CGACC CAG GAT AAC CCT CA-3' (SEQ ID NO:38); qc-h37asp, 5'-AGA TAC TGG GGC CCA GGACTC CGT GCT GAC CCA AA-3' (SEQ ID NO:39); qc-v39ile, 5'-TGG GGC CCA GCA CTC CATCCT GAC CCA AAA TCC TG-3' (SEQ ID NO:40); and qc-a57ile, 5'-TGC CTG GGT CCA AGG GATTAC TGG AGG AAA GCG GT-3' (SEQ ID NO:41), respectively.

Mutated gag-pro-pol plasmids (along with pMD.M (4070A) and pLLRN) were transfected into HEK-293T cells with LIPOFECTAMINE™ 2000 (INVITROGEN™). After 2 days, virus supernatant was collected and the virus stability assayed by comparing virus transduction of luc before and after 24-hour, 37° C. incubation.

EXAMPLE 2

Selection of MLV Mutants with Improved Stability

Amphotropic MLV was mutated by passaging pA14, encoding the MLV genome, in a bacterial mutator strain, XL1-Red (Low, et al. (1996) *J. Mol. Biol.* 260:359-368). The theoretical library size, determined by the population of XL1-Red cells in culture, was greater than 10$^{11}$ clones when counted by limiting dilution, but the experimental virus library size was limited by number of producer cells transfected. With transfection efficiencies of 50-80% for HEK-293 cells and 3×10$^6$ cells at transfection, the effective size of the library was >10$^6$ variant viruses. Viruses produced from the mutated pA14 library exhibited ~50% of the titer of viruses produced using the wild-type vector.

The strategy for selection of more stable viruses was as follows. Viruses were generated by lipofection of the mutated pA14 library into HEK-293 cells. Because many plasmids can enter a given cell during transfection, each cell can produce multiple virus variants. To restore the genotype-phenotype linkage, the "primary" mutant virus library, generated by transfection of the pA14 library, was used to infect naïve HEK-293 cells at a relatively low multiplicity of infection. The library was selected for more stable variants by incubation of the virus suspension at 37° C. for 12 hours. The 12-hour incubation time period was chosen based on the measured infectivity half-life of 6.8 hours at 37° C. for wild-type MLV (r=0.958), consistent with reported values (Kotani, et al. (1994) supra; Andreadis, et al. (1997) supra; Le Doux, et al. (1999) supra; Merten (2004) supra). Thus, a 12-hour incu-

TABLE 1

| Primer Name | Sequence (5'->3') | SEQ ID NO: |
|---|---|---|
| qc1952pro-f | GGT TGT GGG ACC AAG GCC ACA GCC CCT GCA AGT GC | 19 |
| qc1952trp-f | GGT TGT GGG ACC AAG GTG GCA GCC CCT GCA AGT GC | 20 |
| qc1952ser-f | GGT TGT GGG ACC AAG GTC ACA GCC CCT GCA AGT GC | 21 |
| qc1952cys-f | GGT TGT GGG ACC AAG GTG CCA GCC CCT GCA AGT GC | 22 |
| qc1952his-f | GGT TGT GGG ACC AAG GCA CCA GCC CCT GCA AGT GC | 23 |
| qc1952lys-f | GGT TGT GGG ACC AAG GAA ACA GCC CCT GCA AGT GC | 24 |
| qc1952asp-f | GGT TGT GGG ACC AAG GGA TCA GCC CCT GCA AGT GC | 25 |
| qc1952gln-f | GGT TGT GGG ACC AAG GCA ACA GCC CCT GCA AGT GC | 26 |
| qc1952ala-f | GGT TGT GGG AGC AAG GGC ACA GCC CCT GCA AGT GC | 27 |
| qc1952val-f | GGT TGT GGG ACC AAG GGT ACA GCC CCT GCA AGT GC | 28 |
| qc1952leu-f | GGT TGT GGG ACC AAG GCT ACA GCC CCT GCA AGT GC | 29 |
| qc1952ile-f | GGT TGT GGG ACC AAG GAT ACA GCC CCT GCA AGT GC | 30 |
| qc1952thr-f | GGT TGT GGG ACC AAG GAC ACA GCC CCT GCA AGT GC | 31 |
| qc1952met-f | GGT TGT GGG ACC AAG GAT GCA GCC CCT GCA AGT GC | 32 |
| qc1952arg-f | GGT TGT GGG ACC AAG GCG ACA GCC CCT GCA AGT GC | 33 |
| qc1952asn-f | GGT TGT GGG ACC AAG GAA CCA GCC CCT GCA AGT GC | 34 |
| qc1952phe-f | GGT TGT GGG ACC AAG GTT CCA GCC CCT GCA AGT GC | 35 |
| qc1952tyr-f | GGT TGT GGG ACC AAG GTA CCA GCC CCT GCA AGT GC | 36 |

bation period spans nearly two half-lives and allows only ~30% of mutants with wild-type stability to persist. Variant or mutant viruses exhibiting poorer stability were depleted, while variants possessing improved stability were enriched. After incubation, the variant virus supernatant was passaged on naïve HEK-293 cells for infection and amplification to ensure that selected variants retain infectivity. Repeated cycles of incubation and infection gradually enriched the population of variants having improved stability and concurrently depleted the wild-type and less-stable variants.

After seven rounds of incubation and infection, a mutant population with $t_{1/2}$=11.4 hours was obtained (r=0.993). Control selection experiments with non-mutated pA14 were performed in parallel, and the virus supernatant of the control contained no measurable virus activity at round seven, indicating that wild-type virus was completely depleted.

The selected viruses from round 7 were subjected to 4 additional rounds of the 12-hour, 37° C. incubation and infection to determine whether further enrichment was possible. Measurement of the fraction remaining after a 24 hour 37° C. incubation period revealed that the thermostability of the mutant virus supernatants at rounds 7 and 11 were similar, indicating that no further improvement was apparent. To identify even more stable mutants from the improved mutant population of round 7, an additional 4 rounds of 24-hour 37° C. incubation and infection were performed. Again, the virus supernatants from rounds 0 (i.e., round 7 from 12 hour, 37° C. population) and 4 possessed similar stabilities with this longer 24-hour incubation modification.

EXAMPLE 3

Isolation and Characterization of Mutant MLV

To determine if the variant virus population remaining after selection was a heterogeneous mixture of viruses with improvements of varying degrees or a relatively homogeneous population of similarly improved variants, individual clones were isolated from the selected variant population. Mutations in the env coding region were expected, in particular mutations modifying the SU-TM interaction, as observed instability of MLV is attributed to a labile SU-TM interaction. Therefore, the initial search for mutations was limited to the Env protein sequence. Fifty-three env clones were isolated and tested for retention of infectivity after 24-hour incubation at 37° C. None of the env clones appeared to exhibit the improved stability present in the mutant population. Accordingly, the functional mutation(s) appeared to occur elsewhere in the MLV genome outside env. Because the mutator strain employed did not localize mutations to the envelope region but mutated the entire pA14 plasmid, seven gag-pro-pol clones were analyzed, and all were found to be significantly more stable than the parent virus, the titer of which decreased to less than 15% after 24 hours (nearly 3 half-lives).

Sequence analysis of the gag-pro-pol region of four of the thermostable clones all showed the same mutation occurring at 1952 bp from the start of gag, in the pro gene, corresponding to a Gly→Glu substitution at residue 119 (Gly119Glu) in the MLV protease (PR) encoded by pro (FIG. 1). To confirm that this mutation was responsible for enhanced stability, the Gly119Glu mutation was introduced into the wild-type pNC-gag-pol plasmid by site-directed mutagenesis. The Gly119Glu mutation alone produced the enhanced virus stability found in the selected population and isolated variants, resulting in a half-life of ~13.9 hours at 37° C. (FIG. 3). Moreover, the Gly119Glu-PR mutant exhibited improved stability with wild-type envelope protein.

Figure 4:
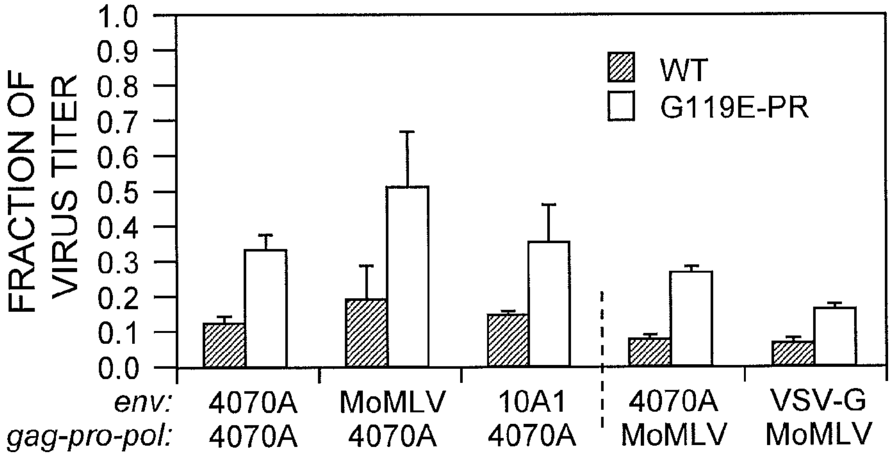
FIG. 4 shows the effect of Gly119Glu-PR substitution on various pseudotypes and strains of MLV, determined as fraction of virus titer remaining after incubation of virus supernatant for 24 hours at 37° C. (n=3; error bars represent standard deviation). Viruses were generated with 4070A, Moloney (MoMLV), 10A1 or VSV-G Env proteins and with gag-pro-pol genes originating from strain 4070A or MoMLV, as shown. Virus displaying 4070A, 10A1 and VSV-G Env were tittered on HEK-293 cells; viruses displaying MoMLV Env were tittered on NIH3T3 cells.

Because the functional mutation was found in PR, the stability enhancement was expected to be independent of the strain of Env protein, which determines the virus host range. To determine the effect of the mutated protease on other MLV strains, the amphotropic Env was replaced with ecotropic (Moloney) or 10A1 Env, recognizing mCAT-1 and Pit1/Pit2 receptors, respectively. Ecotropic- and 10A1-pseudotyped MLV were both stabilized by Gly119Glu-PR (FIG. 4). The Gly119Glu substitution was also introduced into the Moloney MLV PR (97% homology, 95% identity to 4070A MLV PR; FIG. 1), generating a similar enhancement in stability as amphotropic and VSV-G envelopes (FIG. 4).

EXAMPLE 4

Enhancement of Virus Production, Titer, and Infection Efficiency

The difficulty of large-scale production and purification of retroviruses represents a challenge for clinical trials and the development of commercially viable therapies (Powell, et al. (2000) supra; Andreadis, et al. (1999) *Biotechnol. Prog.* 15:1-11; Merten (2004) supra). Because of their short half-life, viruses must be harvested frequently. Furthermore, the maximum achievable titer is limited by the short half-life, with the decay of active virus particles competing with the rate of their generation by producer cells (Le Doux, et al. (1999) supra; Andreadis, et al. (2000) *J. Virol.* 74:1258-1266). An increase in virus half-life was expected to improve both yield and titer, provided the means of stabilization, an amino acid substitution in this case, does not reduce viral protein expression or impede virus assembly.

Figure 5:
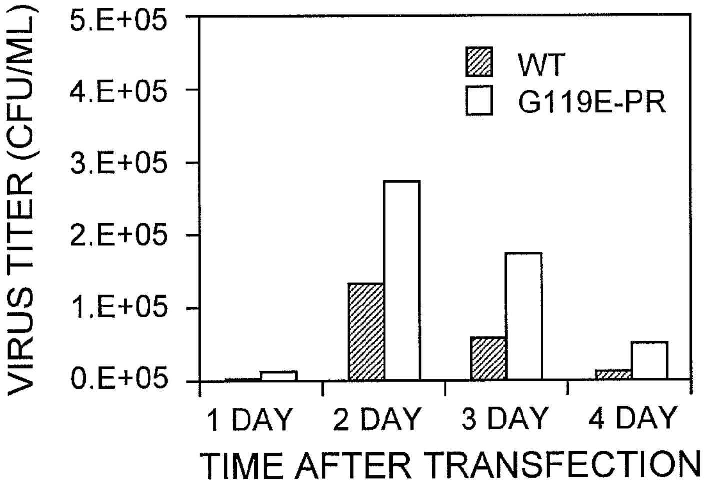
FIG. 5 shows the production of wild-type (wt) and Gly119Glu-PR MLV. Virus was produced in HEK-293T cells after transfection with pMDM(4070A), pNCgag-pol or pNCgag-pol-Gly119Glu, and pLZCX2. The supernatant was collected every 24 hours after transfection and replaced with fresh growth medium. Virus titer in the supernatant was determined by limiting dilution (n=2; bars represent average titer).

Virus production and titer are related; virus production refers to the total active virus output over the duration of the virus collection period, while virus titer measures the number of active virus particles per unit volume, usually reported in transducing or colony-forming units per mL (TU/mL or CFU/mL). To compare production and titer for wild-type and Gly119Glu-PR MLV, equal amounts of wild-type pNCgag-pol (encoding wild-type PR) or pNCgag-pol-Gly119Glu (encoding Gly119Glu-PR) were transfected into HEK-293T cells, and virus-containing supernatant was collected 1 to 4 days post-transfection. Both titer and total virus production were increased on each day for Gly119Glu-PR-containing MLV (FIG. 5). Titers for Gly119Glu-PR MLV were improved by 2- to 4-fold over wild-type MLV at each day during the 4 days of virus harvesting, representing a 2.4-fold increase in total active virus produced. These results indicate that expression and assembly of mutant MLV were not hindered by the mutation in PR, and that the increases in titer and total active virus production was attributed to the longer half-life of the variant virus. While titer was not optimized, it is contemplated that incorporation of the mutant MLV into more optimal packaging cell lines or producer systems will yield even higher titers and production levels.

Consistent with the results at 37° C., the mutated virus also maintained activity for longer periods at 4° C., with half-lives of 17 and 43 days for wild-type and mutant MLV, respectively. Freezing and thawing of virus samples has been shown to decrease virus titer by ~50% (Kwon, et al. (2003) *J. Virol.* 77:5712-5720; Abe, et al. (1998) *J. Virol.* 72:6536-6361). These data indicate that storage of virus samples at 4° C. may be desired over freezing at −80° C. for periods shorter than one month. Thus, another advantage of the variant MLV is the ability to store Gly119Glu-PR MLV at 4° C. rather than freezing at −80° C. for periods up to one month.

Figure 6:
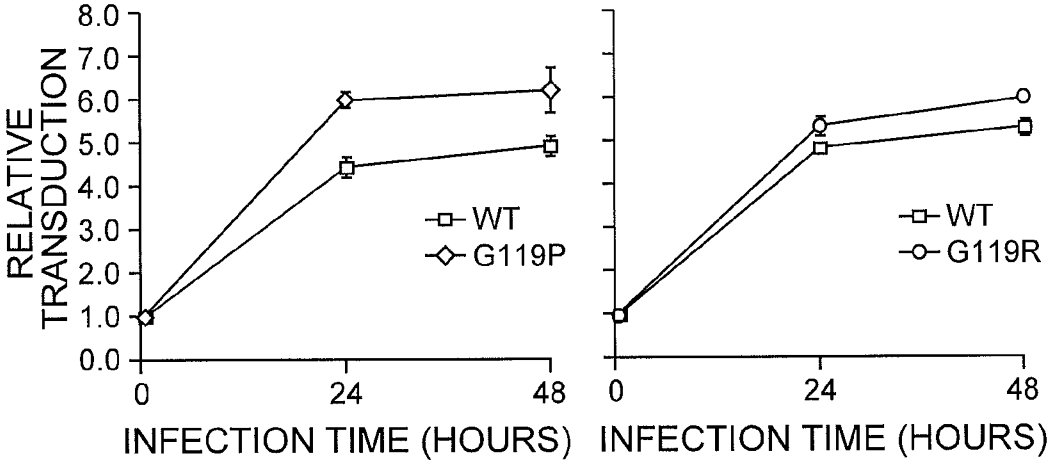
FIG. 6 shows a comparison of transduction efficiency for wild-type and mutant PR MLVs. Wild-type (wt) and Gly119Pro or Gly119Arg mutant virus transduction efficiency was compared in HEK-293 cells after 24-hour and 48-hour infection times. Fresh virus was added after 24 hours for the 48-hour infection. A brief 30 minute pulse infection measured an initial titer that minimized decay for both the wild-type and mutant MLV. In both cases, the mutant MLV maintained higher transduction levels than the wild-type virus (n=3; error bars represent standard deviation).

Retrovirus transduction efficiency is restricted in that retroviral particles are inherently unstable and decay quickly both in culture medium (Le Doux, et al. (1999) supra; Merten, et al. (2004) supra) and after internalization into cells (Andreadis, et al. (1997) *J. Virol.* 71:7541-7548). With such short half-lives, retroviruses lose activity during the time it takes to diffuse through culture medium and reach the target cells (Andreadis, et al. (2000) *J. Virol.* 74:1258-1266). Improvements in virus half-life should allow the mutant virus more time to diffuse and longer distances to travel for successful infection, thereby increasing transduction efficiency. Virus transduction for wild-type and Gly119Pro or Gly119Arg was compared in HEK-293 cells after 24-hour and 48-hour infection periods, with virus replenished after 24 hours during the 48-hour infection period (FIG. 6). A brief 30 minute pulse infection measured an initial titer with minimum decay for both the wild-type and mutant MLV to normalize for different initial titers. Higher transduction levels were obtained with the Gly119Pro and Gly119Arg mutants after both 24-hour and 48-hour infection periods. Moreover, transduction of the mutant MLV after 24 hours was higher than wild-type virus transduction even after the 48-hour serial infection period. Thus, by improving the virus half-life it may be possible to obtain adequate gene transfer in less time and with less vector, potentially leading to safer and more efficient gene therapy.

It is evident that the MLV envelope protein plays a key role in virus stability, at least in response to physical stress. For example, MLV has been made more resistant to ultracentrifugation by pseudotyping with VSV-G (Burns, et al. (1993) supra; Yee, et al. (1994) supra) or by DNA shuffling of ecotropic envelope genes (Powell, et al. (2000) supra). As one might expect, the Gly119Glu-PR MLV, bearing wild-type env, remained sensitive to freeze/thaw and ultracentrifugation physical stresses.

EXAMPLE 5

Site-Saturation Mutagenesis

Single base mutations were scattered throughout the 5.2 kb gag-pro-pol sequences, averaging ~1 substitution per 1600 bases for the four clones analyzed. With a mutation frequency of ~0.063%, the likelihood of more than one mutation within a region of three bases was very small. Thus, with single base mutations to codons and the degeneracy of the genetic code, random mutagenesis typically can only access ~6 of the 19 possible amino acid substitutions (Drummond, et al. (2005) *J. Mol. Biol.* 350:806-816; Zhao, et al. (1999) In: *Manual of Industrial Microbiology and Biotechnology*, Demain & Davies, Editors. ASM Press, Washington D.C., pp. 597-604).

The beneficial Gly119Glu-PR mutation corresponded to a g→a nucleotide substitution at 1952 bp after the start of the MLV gag gene. The codon for glycine at residue 119 is gga; a gaa codon from the point mutation caused the glutamic acid substitution for Gly119Glu-PR. The possible amino acids that can be obtained at position 119 in the MLV PR by single nucleotide substitution of the wild-type codon gga encoding Gly are: aga>Arg, gaa>Glu, ggt>Gly, tga>STOP, gta>Val, ggc>Gly, cga>Arg, gca>Ala, and ggg>Gly. Only four other amino acids (Ala, Val, Arg, Glu) and a stop codon are accessible by single point mutations at 119. Accordingly, the effect of all possible mutations was determined. Applying site-saturation mutagenesis, the remaining Gly119-PR MLV mutants were screened for stability.

Figure 7:
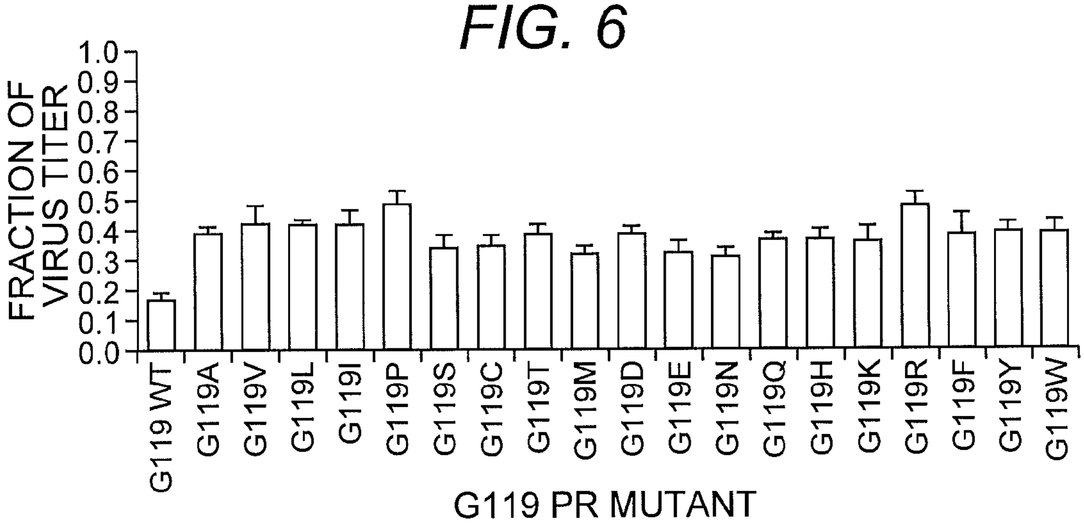
FIG. 7 shows saturation mutagenesis of residue 119 in MLV PR. Each amino acid was substituted in place of wild-type Gly at position 119 in the PR, and all mutants were found to possess higher thermostability than Gly at this site.

The first two MLV protease mutants that were constructed after identifying Gly119Glu-PR were proline and tryptophan. These were chosen because of their uniqueness compared to the other amino acids; proline is the only cyclic amino acid, and tryptophan has one of the largest side chains. Twenty-four hour, 37° C. stability screens indicated a higher stability for both mutants than for the Gly119Glu-PR mutant (FIG. 7). That proline would be able to extend the half-life of MLV to almost 24 hours was unexpected, and therefore other mutants of Gly119-PR were assessed.

FIG. 7 shows stability screens for all 20 amino acids at position 119 of the MLV PR. Glycine, the wild-type residue, produced the least thermostable MLV. To ensure that the improved stability seen in the Gly119-PR mutants was not an artifact of the experimental setup, the Gly119Pro-PR mutant was reverted back to wild-type to restore wild-type activity from an improved mutant PR. Site-directed mutagenesis of the Pro119Pro mutant back to wild-type returned the MLV back to the least thermostable wild-type form.

General trends in the amino acid substitutions indicated that all of the nonpolar aliphatic side chains except glycine, Ala, Val, and Ile, appeared more stable than most of the other substitutions. Another observation was that the Glu substitution, corresponding to the Gly119Glu-PR mutant, appeared only average or below average in terms of improving stability. The most stable MLV mutants were found with Pro, Arg, and Ile amino acid substitutions in PR, and the acidic and amide groups (Asp, Glu, Asn, and Gln) offered the most variability within the amino acid families in stabilizing the virus.

Two of the most stable Gly119-PR mutants from saturation mutagenesis were analyzed in more detail. Virus decay was measured for Gly119Pro-PR and Gly119Arg-PR MLV. Consistent with estimations based on the fraction present after the 24 hours at 37° C. stability screens, the half-lives were extended to ~24 hours for both proline and arginine PR mutants. These data indicate that the most stable MLV mutants improve the 37° C. half-life of wild-type MLV by as much as 4-fold.

EXAMPLE 6

Other Mutations which Increase MLV Half-Life

Figure 8:
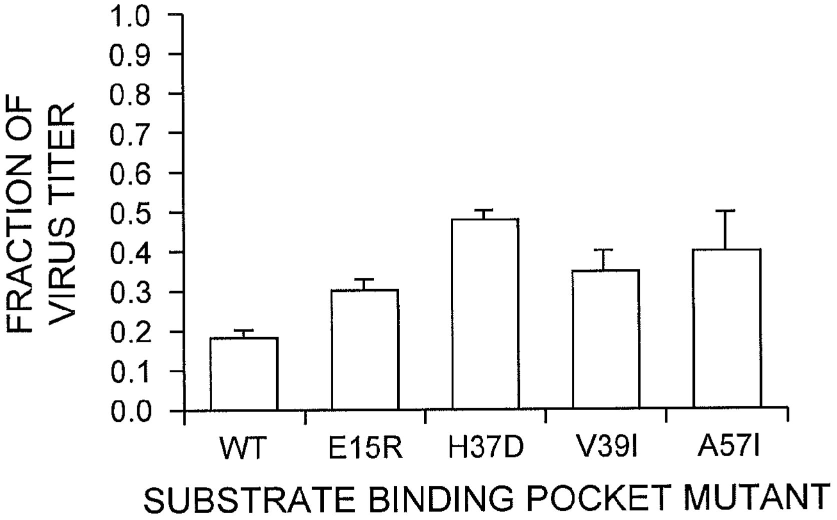
FIG. 8 shows that mutagenesis of residues at positions 15, 37, 39, and 57 of MLV PR increases the thermostability of MLV as compared to wild-type (wt).

Single mutations to the MLV protease were introduced by site-directed mutagenesis. The four sites of the MLV PR modified were positions 15, 37, 39, and 57 (Glu15Arg, His37Asp, Val39Ile, Ala57Ile). These single mutants were selected based on MLV PR mutational analysis identifying mutations that modify the substrate binding pocket of MLV PR (Menendez-Arias, et al. (1995) *J. Biol. Chem.* 270:29162-29168). Viruses with mutant PRs were prepared and the stability screening was carried out as disclosed herein, by comparing virus activity before and after incubation for 24 hours at 37° C. (FIG. 8). The higher fractions remaining after the 24 hour, 37° C. incubation for the mutants compared to wild-type indicates that, like mutations at 119, these mutations appear to make the 37° C. virus half-life longer. This indicates that other mutations (single or multiple) exist in the retroviral protease that extend virus thermostability.

Figure 9:
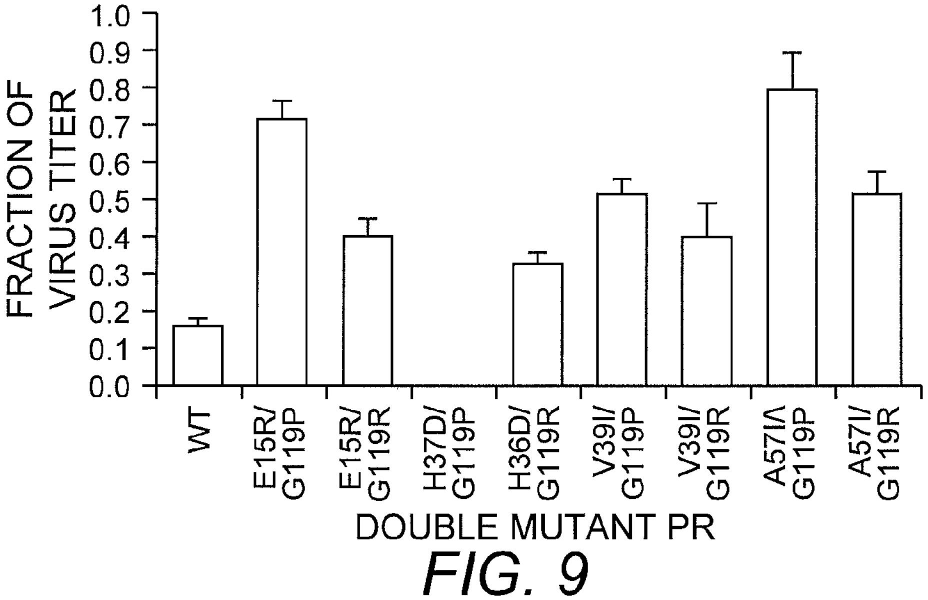
FIG. 9 shows virus stability of double mutants by plotting the fraction of virus titer remaining after incubation of virus supernatant for 24 hours at 37° C. The wild-type (wt) virus provided the most drastic reductions in titer compared to all single PR mutants and all but one of the double mutants ($n \geqq 3$; error bars represent standard deviation).

To determine if additive effects on stability could be obtained with double mutants, Gly119Pro or Gly119Arg mutations were incorporated into the substrate binding pocket PR mutants. Seven of the eight double mutants resulted in higher activity fractions remaining compared to the wild-type (FIG. 9). The largest fractions were measured with Glu15Arg/Gly119Pro and Ala57Ile/Gly119Pro mutants, while the other functional double mutants had stabilities similar to Gly119Pro and Gly119Arg. Additionally, stability enhancement was observed for MLV containing the mutant PRs and pseudotyped with VSV-G envelope protein.

Figure 10:
FIG. 10 shows a comparison of virus production for wild-type and mutant PR MLVs. Virus was produced in HEK-293T cells after transfection with wild-type (wt) or mutant virus DNA. Retroviral supernatant was collected every 24 hours and replaced with fresh growth media. Virus titer was determined by transduction of luc with the luciferase assay (n=3; error bars represent standard deviation).

The prevalence of seemingly beneficial mutations indicates that a "compromised" PR, in fact, may lead to prolonged virus activity. The viral PR plays a key role in the proteolytic processing of viral proteins indicating that mutations to PR affect virus assembly and/or maturation. To consider this, virus production and titer were examined for Gly119Pro, Gly119Arg, and all double mutants. Wild-type or mutant PR virus DNA was transfected into HEK-293T cells, and titers of virus-containing supernatant harvested 1 to 4 days after transfection were measured (FIG. 10). Titers of wild-type MLV peaked at 2 days after transfection. Glu25Arg- and His37Asp-containing double mutants achieved titers that were less than 10% of wild-type. Ala57Ile/Gly119Pro virus titers increased over the 4-day study, but were only ~10% of wild-type over the 4-day collection period, and Val39Ile/Gly119Pro titers were comparable to wild-type. Virus titers for Ala57Ile/Gly119Arg, Val39Ile/Gly119Arg, Gly119Pro, and Gly119Arg mutants were improved over the wild-type, however, with Val39Ile/Gly119Arg and Gly119Arg mutants exceeding wild-type virus production by more than 2-fold over the 4 days. In addition, Gly119Arg titers were roughly equivalent on days 2 and 3, while Val39Ile/Gly119Arg and Ala57Ile/Gly119Arg reached a maximum titer after 3 days. This slower virus production is consistent with the PR mutations affecting virus assembly or maturation.

Figure 11:
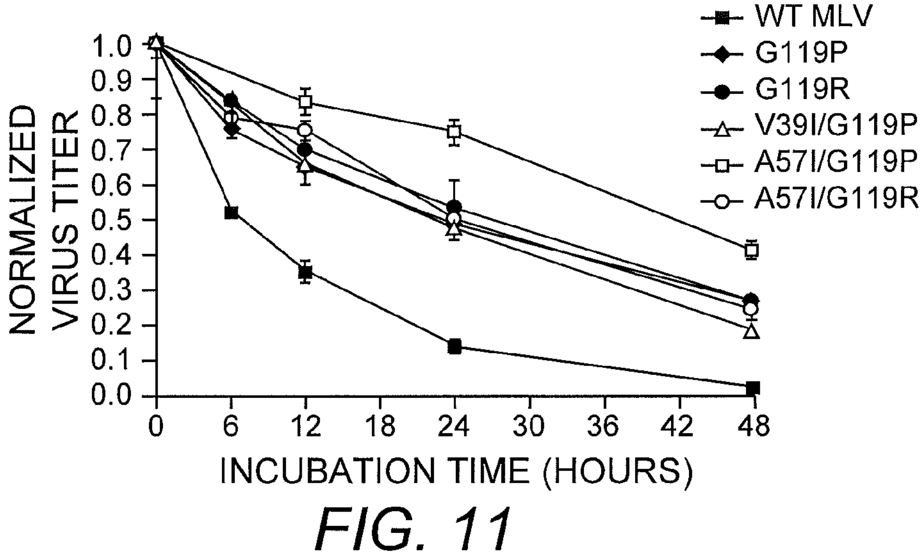
FIG. 11 shows a comparison of virus decay for wild-type and mutant PR MLVs. Viruses in conditioned medium were incubated at 37° C. for the times shown, and virus activity was measured by luciferase assay and normalized to the 0 hour sample with no incubation. The wild-type (wt) virus half-life was ~8 hours, while those of the improved mutants (Gly119Pro, Gly119Arg, Val39Ile/Gly119Pro, Ala57Ile/Gly119Arg) were ~24 hours. The Ala57Ile/Gly119Pro mutant exhibited a half-life of ~40 hours at 37° C. (n=3; error bars represent standard deviation).

Based on the fraction of virus titer remaining from the 24 hours, 37° C. stability screens and simple virus decay kinetics, the virus half-lives (at 37° C.) can be estimated for the mutants with improved stability. With fractions of Gly119Pro, Gly119Arg, Val39Ile/Gly119Pro and Ala57Ile/Gly119Arg remaining after incubation equal to ~0.5 (FIGS. 7 and 9), the projected half-life for these MLV mutants is ~24 hours at 37° C. This value was in agreement with virus decay experiments (FIG. 11), and represents the longest reported half-life for this widely used retroviral vector. The Ala57Ile/Gly119Pro mutant exhibited a half-life of ~40 hours at 37° C., but with lower titers.

EXAMPLE 7

Model for Mutant Virus Selection

Based on the properties of the improved Gly119Glu-PR mutant, a simple mathematical model was developed for the selection process. The basic expression for virus activity V was introduced as a function of time t:

$$V(t)=V_0e^{-kt} \quad (1)$$

where $V_0$ was the initial amount of active virus and k was virus decay constant. By manipulation, the virus half-life, $t_{1/2}$, when V was equal to half of $V_0$, and k were related by $$t_{1/2}=\frac{\ln 2}{k} \text{ and } k=\frac{\ln 2}{t_{1/2}}. \quad (2)$$

The total virus amount, $V^{tot}$, was defined as the sum of $V^{wt}$ and $V^{mut}$, wild-type and improved mutant virus populations, respectively:

$$V^{tot}=V^{wt}+V^{mut}\leq 10^6 \quad (3).$$

It was assumed that $v^{wt}$ was not only wild-type, but mutants with wild-type and near wild-type stability. Thus, $V^{mut}$ was the small subset of mutants that were considered to be improved, with the non-improved mutants absorbed by $V^{wt}$. $V^{tot}$ was bounded by a maximum virus titer $10^6$ CFU/mL, consistent with reported values in literature (Merten (2004) supra). At the onset of selection, i.e., round 0, the initial titer $V_0^{tot}$ was $10^6$, and rearranging equation (3) it was observed $$V_0^{wt}=V_0^{tot}-V_0^{mut}, \text{ or } V_0^{wt}=10^6-V_0^{mut} \quad (4)$$

where $V_0^{wt}$ and $V_0^{mut}$ are the initial wild-type and mutant virus titers, respectively. It was expected that the wild-type population would be larger in early rounds, before enrichment of improved mutants occurred.

The instant selection process included a 12 hour, 37° C. incubation step, followed by infection of target cells. For simplicity, the wild-type half-life, $t_{1/2}^{wt}$, was considered ~6 hours and the improved mutant virus half-life, $t_{1/2}^{mut}$, to be ~12 hours. Thus, at round 1 of selection it was expected that ~25% and ~50% of wild-type and mutant viruses, respectively, were remaining after 12-hour incubation, $$\frac{1}{4}V_0^{wt} \text{ and } \frac{1}{2}V_0^{mut} \quad (5)$$

When the viruses from equation (5) are applied to infect naïve target cells for propagation, with $G^{wt}$ and $G^{mut}$ representing the rates of virus generation (per infected cell) for the wild-type and mutant MLV, respectively, after round 1(n=1) the following is obtained $$V_1^{wt}=\left(\frac{1}{4}V_0^{wt}\right)G^{wt} \text{ and } V_1^{mut}=\left(\frac{1}{2}V_0^{mut}\right)G^{mut} \quad (6)$$

Values for $G^{wt}$ have been reported (Le Doux, et al. (1999) supra), and as disclosed herein it was found that Gly119Glu-PR improved mutant virus production was enhanced overall by 2.4-fold. Thus, conservatively, the substitution $G^{mut}=2G^{wt}$ can be made, and equation 6 becomes $$V_1^{wt}=\left(\frac{1}{4}V_0^{wt}\right)G^{wt} \text{ and } V_1^{mut}=(V_0^{mut})G^{wt} \quad (7)$$

Similarly, after round 2 (n=2) of incubation and infection, it is found $$V_2^{wt}=\left(\frac{1}{4}\left(\frac{1}{4}V_0^{wt}\right)G^{wt}\right)G^{wt} \text{ and } V_1^{mut}=\left(\frac{1}{2}(V_0^{mut})G^{wt}\right)2G^{wt}. \quad (8)$$

Continuing, $V_n^{wt}$ and $V_n^{mut}$ were generalized for n rounds of 12 hour, 37° C. incubation and infection by and $$V_n^{wt}=\left(\frac{1}{4}G^{wt}\right)^n V_o^{wt} \text{ and } V_n^{mut}=(G^{wt})^n V_0^{mut}. \quad (9)$$

Now, with the expressions in equation (9), the concentrations for the wild-type and improved mutant viruses were plotted at each round of selection. Setting $V_0^{mut}$, the value of $V_0^{wt}$ is solved by equation (4), and the value of $G^{wt}=3$ (viruses/cell) was chosen from the literature (Le Doux, et al. (1999) supra).

Accordingly, it was determined how the initial fraction of improved mutants present in round 0, at the start of selection, affected the enrichment of mutants. The values for $V_0^{mut}$ were set at 10%, 1%, 0.1%, and 0.01% of $V_0^{tot}$, where $V_0^{tot}$ was $10^6$. It was observed that as the initial fraction of improved mutants decreased, more rounds of selection were needed before the improved mutant population equaled the wild-type concentration. In all cases shown, the mutant eventually became the dominant virus population as the selection progressed. While an initial value of 10% improved mutants in the initial population was improbable, this was meant to illustrate the trend and serve as an upper bound. Where $V_0^{mut}$ was 0.01% of the initial population, the model predicted that more than 8 rounds of selection were needed before the wild-type was removed and enrichment of the mutant occurred. Experimentally, it was found that the wild-type control was cleared by round 7 of selection. Considering that the improved mutant population at round 7 did not benefit or appear to become further enriched by continued selection, it was surmised that the fraction of improved mutants in the initial mutant MLV library was between 1% and 0.1% of the total virus population at the onset of selection. It was noted that the curves were the same whether $V_0^{tot}$ was $10^6$ or $10^5$, the latter being the case where the titers were lower than the estimated values. Of interest was whether an initial population of $10^5$ viruses/mL was sufficient to thoroughly search the library for improved mutants.

Unexpectedly, the model predicted the competition between wild-type and mutant viruses due to the physically valid $10^6$ restriction placed on the total virus concentration, $V_0^{tot}$. Experimentally, there were a limited number of target cells for infection and propagation. When the value of exceeded $10^6$, $V^{wt}$ and $V^{mut}$ were scaled to total $10^6$ based on the wild-type and mutant virus fractions in the population exceeding $10^6$ given by the formulas in equation (9). Thus, the wild-type was forced to extinction when the mutant was enriched quickly; however, the wild-type was allowed to diminish more slowly when not in competition with mutant virus enrichment.

The wild-type virus generation $G^{wt}$ term was also investigated. While experiments were not carried out to calculate this number, the reported values of 2 to 3 (viruses/cell/day) (Le Doux, et al. (1999) supra) seemed small. Nevertheless, the numbers were consistent with the model. As seen for $V_n^{wt}$ in equation (9), a value for $G^{wt}$ greater than 4 would have offset wild-type decay by the 12 hour, 37° C. incubation step. Thus, wild-type virus able to grow with increasing rounds of selection would be observed, and it would be uncertain whether the mutant could compete for infection and eventually take over the population with its faster generation rate. Experimentally, an increase in the incubation time from 12 hour could be carried out to determine the time needed to cause a dropoff in the wild-type. Alternatively, if $G^{wt}$ were less than 1, the $V_n^{mut}$ term would now drop off with selection, giving the result of no enrichment for the improved mutant. This would be more difficult to overcome experimentally, but the addition of growth factors could be used. Comparing $G^{wt}$ values of 2 and 3 for equation (9), the intersection of wild-type and mutant virus populations occurring at the same location in selection might be unexpected. Enrichment proceeds more rapidly when $G^{wt}$ is 3, and the wild-type population washes out more quickly when the generation term is 2. Note that it becomes much more of a challenge for the mutant to become enriched for when $G^{wt}$ is 2 and $V_0^{mut}$ is 0.1% of the initial virus population $V_0^{tot}$.

The effect of mutant virus generation $G^{mut}$ was also examined. Based on the experimental results with Gly119Glu-PR, $G^{mut}$ was substituted with $2G^{wt}$ to obtain equation (7). It was this factor of 2 that cancelled out the 2-fold decrease by virus decay as seen in equation (5). The cancellation caused the term $V_n^{mut}$ to increase for all n rounds of selection (and $G^{wt}>1$), essential for the enrichment of improved mutants by the instant incubation and selection method. Without the enhanced virus production (i.e., if $G^{mut}=G^{wt}$), $V_n^{mut}$ loses much of its enrichment capability and amplifies slowly. With the initial improved mutants at 1% of $V_0^{tot}$, the mutant virus barely reaches half of its maximum by 10 rounds of selection. Also, if virus production for the mutant was not enhanced, with $G^{mut}=G^{wt}$, a value of 2 or less for virus generation $G^{wt}$ would not allow amplification of the improved mutants by this model. From this, a better understanding of how a much more stable mutant with only average virus production levels, possibly Gly119Arg-PR, might not be selected in the presence of a moderately improved mutant like Gly119Glu-PR, with enhanced virus generation. In the same way, an improved mutant with worse generation kinetics than wild-type would have little chance of being enriched.

Further, upon withdrawal of the 6 hour and 12 hour half-life simplifications used in this analysis, the more general form of equation (9) becomes $$V_n^{wt} = (e^{-k_{wt}t}G^{wt})^n V_0^{wt} \text{ and } V_n^{mut} = (e^{-k_{mut}t}G^{mut})^n V_0^{mut} \qquad (10)$$

where $k_{wt}$ and $k_{mut}$ are the wild-type and improved mutant virus decay constants, respectively.

Overall, based on these equations, experimental data, and the literature, an estimation of between 1% and 0.1% was obtained for the fraction of improved mutants initially present in the mutant virus library.

EXAMPLE 8

Mechanisms of Stabilization

The MLV PR contains 125 amino acids and is translated through suppression of an amber termination codon (UAG) at the 3' end of the gag gene (Yoshinaka, et al. (1985) *Proc. Natl. Acad. Sci. USA* 82:1618-1622). Amino acid 119 is located near the carboxyl terminus of the protein. Although the crystal structure for MLV PR has not been solved, crystal structures for other retroviral proteases including HIV-1 (Navia, et al. (1989) *Nature* 337:615-620; Wlodower, et al. (1989) *Science* 245:616-621), HIV-2 (Mulichak, et al. (1993) *J. Biol. Chem.* 268:13103-13109), SIV (Rose, et al. (1993) *Biochemistry* 32:12498-12507), FIV (Wlodower, et al. (1995) *Nat. Struct. Biol.* 2:480-488), EAIV (Gustchina, et al. (1996) *Protein Sci.* 5:1453-1465), and RSV (Miller, et al. *Nature* 337: 576-579) have been determined. The structures of these proteases contain features conserved among retroviral PRs (Coffin (1996) supra; Weber (1989) *Gene* 85:565-566; Wlodawer & Gustchina (2000) *Biochem. Biophys. Acta* 1477: 16-34). In particular, sequence alignment of the MLV PR with the RSV PR(RSV and MLV PR sequences share 51% homology, 24% identity; FIG. 2), containing 124 amino acids, allows qualitative visualization of the Gly119Glu-PR mutation in MLV by mapping the Gly119Glu mutation onto the solved RSV PR structure.

The active form of PR is a homodimer (Wlodawer & Gustchina (2000) supra) with twofold symmetry (Pearl & Taylor (1987) supra). The monomer subunit is enzymatically inactive (Pearl & Taylor (1987) *Nature* 329:351-354). As a result, the Gly119Glu-PR mutation is effectively represented twice in the functional dimer. Crystal structures for HIV and RSV proteases show that the dimer interface contains a four-stranded antiparallel β-sheet composed of the amino- and carboxyl-termini of each monomeric subunit. Furthermore, interactions at the dimer interface are suggested to play a key role in the stability of the protease (Todd, et al. (1998) *J. Mol. Biol.* 283:475-488). A mutation near the C-terminus of each monomer subunit could have considerable consequences with respect to dimer stability by modifying two of the four-strands in the antiparallel β-sheet motif. Furthermore, a double mutation at the dimerization interface has been reported to double the autolysis rate in HIV-1 PR (Kumar, et al. (2002) *Biochem. Biophys. Res. Comm.* 294:395-401). In Gly119Glu-PR, substitution of glycine with glutamic acid replaces the nonpolar glycine with a negatively charged, acidic (p$K_a$ 4.1) residue. Therefore, formation of electrostatic interactions or steric effects in the antiparallel β-sheet may affect the dimer stability.

The primary function of PR is to cleave Gag and Gag-Pro-Pol precursor proteins into the smaller protein products found in mature virus particles after assembly. In the case of MLV, PR has also been discovered to remove a small "R" peptide near the C-terminus of TM that is necessary to allow TM to mediate virus-cell membrane fusion (Rein, et al. (1994) *J. Virol.* 68:1773-1781). If this processing of TM also effects the TM-SU interaction, it is contemplated that one mechanism for the enhanced stability of infectivity is that Gly119Glu-PR is in fact less active, leading to slower generation of the mature (possibly labile) Env. PR may also play a role in early infection. For example, in equine infectious anemia virus (EIAV), PR cleaves the NC protein, which may be required for reverse transcription or integration. Further, cleavage of cellular proteins, such as NF-κB and cytoskeleton proteins, after cell entry may be necessary for infection. In the latter two cases, the stability of PR should be directly correlated with stability of infectivity. Recombinant expression of Gly119Glu-PR (Kumar, et al. (2002) supra; Cheng, et al. (1989) *Proc. Natl. Acad. Sci. USA* 87:9660-9664) or direct purification from retroviruses (Yoshinaka, et. al (1985) supra) is employed to elucidate the nature of the variant protease and the mechanism of stabilization.

What is claimed is:

1. An isolated mutant murine leukemia virus protease comprising an amino acid substitution at position 119 of SEQ ID NO:1.

* * * * *

SEQUENCE LISTING

```
<160> NUMBER OF SEQ ID NOS: 41

<210> SEQ ID NO 1
<211> LENGTH: 125
<212> TYPE: PRT
<213> ORGANISM: Artificial Sequence
<220> FEATURE:
<223> OTHER INFORMATION: Synthetic MLV protease
<220> FEATURE:
<221> NAME/KEY: MISC_FEATURE
<222> LOCATION: (1)..(1)
<223> OTHER INFORMATION: Xaa denotes Ala or Thr
<220> FEATURE:
<221> NAME/KEY: MISC_FEATURE
<222> LOCATION: (8)..(8)
<223> OTHER INFORMATION: Xaa denotes Arg or Gln
<220> FEATURE:
<221> NAME/KEY: MISC_FEATURE
<222> LOCATION: (12)..(12)
<223> OTHER INFORMATION: Xaa denotes Leu or Pro
<220> FEATURE:
<221> NAME/KEY: MISC_FEATURE
<222> LOCATION: (102)..(102)
<223> OTHER INFORMATION: Xaa denotes Asn or Lys
<220> FEATURE:
<221> NAME/KEY: MISC_FEATURE
<222> LOCATION: (115)..(115)
<223> OTHER INFORMATION: Xaa denotes Val or Met
<220> FEATURE:
<221> NAME/KEY: MISC_FEATURE
<222> LOCATION: (118)..(118)
<223> OTHER INFORMATION: Xaa denotes Arg or Met

<400> SEQUENCE: 1

Xaa Leu Asp Asp Gln Gly Gly Xaa Gly Gln Glu Xaa Pro Pro Glu Pro
1               5                   10                  15

Arg Ile Thr Leu Lys Val Gly Gly Gln Pro Val Thr Phe Leu Val Asp
            20                  25                  30

Thr Gly Ala Gln His Ser Val Leu Thr Gln Asn Pro Gly Pro Leu Ser
        35                  40                  45

Asp Lys Ser Ala Trp Val Gln Gly Ala Thr Gly Gly Lys Arg Tyr Arg
    50                  55                  60

Trp Thr Thr Asp Arg Lys Val His Leu Ala Thr Gly Lys Val Thr His
65                  70                  75                  80
```

-continued

```
Ser Phe Leu His Val Pro Asp Cys Pro Tyr Pro Leu Leu Gly Arg Asp
                85                  90                  95

Leu Leu Thr Lys Leu Xaa Ala Gln Ile His Phe Glu Gly Ser Gly Ala
            100                 105                 110

Gln Val Xaa Gly Pro Xaa Gly Gln Pro Leu Gln Val Leu
        115                 120                 125


<210> SEQ ID NO 2
<211> LENGTH: 125
<212> TYPE: PRT
<213> ORGANISM: Murine leukemia virus

<400> SEQUENCE: 2

Ala Leu Asp Asp Gln Gly Gly Arg Gly Gln Glu Leu Pro Pro Glu Pro
1               5                   10                  15

Arg Ile Thr Leu Lys Val Gly Gly Gln Pro Val Thr Phe Leu Val Asp
            20                  25                  30

Thr Gly Ala Gln His Ser Val Leu Thr Gln Asn Pro Gly Pro Leu Ser
        35                  40                  45

Asp Lys Ser Ala Trp Val Gln Gly Ala Thr Gly Gly Lys Arg Tyr Arg
    50                  55                  60

Trp Thr Thr Asp Arg Lys Val His Leu Ala Thr Gly Lys Val Thr His
65                  70                  75                  80

Ser Phe Leu His Val Pro Asp Cys Pro Tyr Pro Leu Leu Gly Arg Asp
                85                  90                  95

Leu Leu Thr Lys Leu Asn Ala Gln Ile His Phe Glu Gly Ser Gly Ala
            100                 105                 110

Gln Val Val Gly Pro Arg Gly Gln Pro Leu Gln Val Leu
        115                 120                 125


<210> SEQ ID NO 3
<211> LENGTH: 125
<212> TYPE: PRT
<213> ORGANISM: Artificial Sequence
<220> FEATURE:
<223> OTHER INFORMATION: Mutant Murine Leukemia Virus

<400> SEQUENCE: 3

Ala Leu Asp Asp Gln Gly Gly Arg Gly Gln Glu Leu Pro Pro Glu Pro
1               5                   10                  15

Arg Ile Thr Leu Lys Val Gly Gly Gln Pro Val Thr Phe Leu Val Asp
            20                  25                  30

Thr Gly Ala Gln His Ser Val Leu Thr Gln Asn Pro Gly Pro Leu Ser
        35                  40                  45

Asp Lys Ser Ala Trp Val Gln Gly Ala Thr Gly Gly Lys Arg Tyr Arg
    50                  55                  60

Trp Thr Thr Asp Arg Lys Val His Leu Ala Thr Gly Lys Val Thr His
65                  70                  75                  80

Ser Phe Leu His Val Pro Asp Cys Pro Tyr Pro Leu Leu Gly Arg Asp
                85                  90                  95

Leu Leu Thr Lys Leu Asn Ala Gln Ile His Phe Glu Gly Ser Gly Ala
            100                 105                 110

Gln Val Val Gly Pro Arg Glu Gln Pro Leu Gln Val Leu
        115                 120                 125


<210> SEQ ID NO 4
<211> LENGTH: 125
```

-continued

<212> TYPE: PRT
<213> ORGANISM: Moloney Murine Leukemia Virus

<400> SEQUENCE: 4

Thr Leu Asp Asp Gln Gly Gly Gln Gly Gln Glu Pro Pro Pro Glu Pro
1 5 10 15

Arg Ile Thr Leu Lys Val Gly Gly Gln Pro Val Thr Phe Leu Val Asp
20 25 30

Thr Gly Ala Gln His Ser Val Leu Thr Gln Asn Pro Gly Pro Leu Ser
35 40 45

Asp Lys Ser Ala Trp Val Gln Gly Ala Thr Gly Gly Lys Arg Tyr Arg
50 55 60

Trp Thr Thr Asp Arg Lys Val His Leu Ala Thr Gly Lys Val Thr His
65 70 75 80

Ser Phe Leu His Val Pro Asp Cys Pro Tyr Pro Leu Leu Gly Arg Asp
85 90 95

Leu Leu Thr Lys Leu Lys Ala Gln Ile His Phe Glu Gly Ser Gly Ala
100 105 110

Gln Val Met Gly Pro Met Gly Gln Pro Leu Gln Val Leu
115 120 125

<210> SEQ ID NO 5
<211> LENGTH: 99
<212> TYPE: PRT
<213> ORGANISM: Human immunodeficiency virus type 1

<400> SEQUENCE: 5

Pro Gln Ile Thr Leu Trp Lys Arg Pro Leu Val Thr Ile Lys Ile Gly
1 5 10 15

Gly Gln Leu Lys Glu Ala Leu Leu Asp Thr Gly Ala Asp Asp Thr Val
20 25 30

Ile Glu Glu Met Ser Leu Pro Gly Arg Trp Lys Pro Lys Met Ile Gly
35 40 45

Gly Ile Gly Gly Phe Ile Lys Val Arg Gln Tyr Asp Gln Ile Ile Ile
50 55 60

Glu Ile Cys Gly His Lys Ala Ile Gly Thr Val Leu Val Gly Pro Thr
65 70 75 80

Pro Val Asn Ile Ile Gly Arg Asn Leu Leu Thr Gln Ile Gly Cys Thr
85 90 95

Leu Asn Phe

<210> SEQ ID NO 6
<211> LENGTH: 99
<212> TYPE: PRT
<213> ORGANISM: Human immunodeficiency virus type 2

<400> SEQUENCE: 6

Pro Gln Phe Ser Leu Trp Lys Arg Pro Val Val Thr Ala Tyr Ile Glu
1 5 10 15

Gly Gln Pro Val Glu Val Leu Leu Asp Thr Gly Ala Asp Asp Ser Ile
20 25 30

Val Ala Gly Ile Glu Leu Gly Asn Asn Tyr Ser Pro Lys Ile Val Gly
35 40 45

Gly Ile Gly Gly Phe Ile Asn Thr Lys Glu Tyr Lys Asn Val Glu Ile
50 55 60

Glu Val Leu Asn Lys Lys Val Arg Ala Thr Ile Met Thr Gly Asp Thr
65 70 75 80

-continued

Pro Ile Asn Ile Phe Gly Arg Asn Ile Leu Thr Ala Leu Gly Met Ser
85 90 95

Leu Asn Leu

<210> SEQ ID NO 7
<211> LENGTH: 99
<212> TYPE: PRT
<213> ORGANISM: Simian immunodeficiency virus

<400> SEQUENCE: 7

Pro Gln Phe Ser Leu Trp Arg Arg Pro Val Val Thr Ala His Ile Glu
1 5 10 15

Gly Gln Pro Val Glu Val Leu Leu Asp Thr Gly Ala Asp Asp Ser Ile
20 25 30

Val Thr Gly Ile Glu Leu Gly Pro His Tyr Thr Pro Lys Ile Val Gly
35 40 45

Gly Ile Gly Gly Phe Ile Asn Thr Lys Glu Tyr Lys Asn Val Glu Ile
50 55 60

Glu Val Leu Gly Lys Arg Ile Arg Gly Thr Ile Met Thr Gly Asp Thr
65 70 75 80

Pro Ile Asn Ile Phe Gly Arg Asn Leu Leu Thr Ala Leu Gly Met Ser
85 90 95

Leu Asn Phe

<210> SEQ ID NO 8
<211> LENGTH: 116
<212> TYPE: PRT
<213> ORGANISM: Feline immunodeficiency virus

<400> SEQUENCE: 8

Tyr Asn Lys Val Gly Thr Thr Thr Thr Leu Glu Lys Arg Pro Glu Ile
1 5 10 15

Leu Ile Phe Val Asn Gly Tyr Pro Ile Lys Phe Leu Leu Asp Thr Gly
20 25 30

Ala Asp Ile Thr Ile Leu Asn Arg Arg Asp Phe Gln Val Lys Asn Ser
35 40 45

Ile Glu Asn Gly Arg Gln Asn Met Ile Gly Val Gly Gly Gly Lys Arg
50 55 60

Gly Thr Asn Tyr Ile Asn Val His Leu Glu Ile Arg Asp Glu Asn Tyr
65 70 75 80

Lys Thr Gln Cys Ile Phe Gly Asn Val Cys Val Leu Glu Asp Asn Ser
85 90 95

Leu Ile Gln Pro Leu Leu Gly Arg Asp Asn Met Ile Lys Phe Asn Ile
100 105 110

Arg Leu Val Met
115

<210> SEQ ID NO 9
<211> LENGTH: 104
<212> TYPE: PRT
<213> ORGANISM: Equine infectious anemia virus

<400> SEQUENCE: 9

Val Thr Tyr Asn Leu Glu Lys Arg Pro Thr Thr Ile Val Leu Ile Asn
1 5 10 15

Asp Thr Pro Leu Asn Val Leu Leu Asp Thr Gly Ala Asp Thr Ser Val
20 25 30

-continued

```
Leu Thr Thr Ala His Tyr Asn Arg Leu Lys Tyr Arg Gly Arg Lys Tyr
        35                  40                  45

Gln Gly Thr Gly Ile Gly Gly Val Gly Gly Asn Val Glu Thr Phe Ser
    50                  55                  60

Thr Pro Val Thr Ile Lys Lys Lys Gly Arg His Ile Lys Thr Arg Met
65                  70                  75                  80

Leu Val Ala Asp Ile Pro Val Thr Ile Leu Gly Arg Asp Ile Leu Gln
                85                  90                  95

Asp Leu Gly Ala Lys Leu Val Leu
            100
```

<210> SEQ ID NO 10
<211> LENGTH: 124
<212> TYPE: PRT
<213> ORGANISM: Rous sarcoma virus

<400> SEQUENCE: 10

```
Leu Ala Met Thr Met Glu His Lys Asp Arg Pro Leu Val Arg Val Ile
1               5                   10                  15

Leu Thr Asn Thr Gly Ser His Pro Val Lys Gln Arg Ser Val Tyr Ile
            20                  25                  30

Thr Ala Leu Leu Asp Ser Gly Ala Asp Ile Thr Ile Ile Ser Glu Glu
        35                  40                  45

Asp Trp Pro Thr Asp Trp Pro Val Met Glu Ala Ala Asn Pro Gln Ile
    50                  55                  60

His Gly Ile Gly Gly Gly Ile Pro Met Arg Lys Ser Arg Asp Met Ile
65                  70                  75                  80

Glu Leu Gly Val Ile Asn Arg Asp Gly Ser Leu Glu Arg Pro Leu Leu
                85                  90                  95

Leu Phe Pro Ala Val Ala Met Val Arg Gly Ser Ile Leu Gly Arg Asp
            100                 105                 110

Cys Leu Gln Gly Leu Gly Leu Arg Leu Thr Asn Leu
        115                 120
```

<210> SEQ ID NO 11
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 11
attgcggccg cttacacagt cctgctgacc ac 32

<210> SEQ ID NO 12
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 12
ccgatatctc catgccttgc aaaatggcgt tacttaag 38

<210> SEQ ID NO 13
<211> LENGTH: 30
<212> TYPE: DNA
<213> ORGANISM: Artificial Sequence
<220> FEATURE:
<223> OTHER INFORMATION: Synthetic oligonucleotide -continued

<400> SEQUENCE: 13
tagcggccgc acttgtggtc tcgctgttcc 30

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 14
cgacatacgg ttcctggtct 20

<210> SEQ ID NO 15
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 15
ggttgtggga ccaagggaac agcccctgca agtgc 35

<210> SEQ ID NO 16
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 16
gcacttgcag gggctgttcc cttggtccca caacc 35

<210> SEQ ID NO 17
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 17
ggttatggga ccaatggagc agcccctgca agtgt 35

<210> SEQ ID NO 18
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 18
acacttgcag gggctgctcc attggtccca taacc 35

<210> SEQ ID NO 19
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 19
ggttgtggga ccaaggccac agcccctgca agtgc 35

<210> SEQ ID NO 20

-continued

<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 20
ggttgtggga ccaaggtggc agcccctgca agtgc 35

<210> SEQ ID NO 21
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 21
ggttgtggga ccaaggtcac agcccctgca agtgc 35

<210> SEQ ID NO 22
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 22
ggttgtggga ccaaggtgcc agcccctgca agtgc 35

<210> SEQ ID NO 23
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 23
ggttgtggga ccaaggcacc agcccctgca agtgc 35

<210> SEQ ID NO 24
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 24
ggttgtggga ccaaggaaac agcccctgca agtgc 35

<210> SEQ ID NO 25
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 25
ggttgtggga ccaagggatc agcccctgca agtgc 35

<210> SEQ ID NO 26
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 26

-continued ggttgtggga ccaaggcaac agcccctgca agtgc 35

<210> SEQ ID NO 27
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 27
ggttgtggga ccaagggcac agcccctgca agtgc 35

<210> SEQ ID NO 28
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 28
ggttgtggga ccaagggtac agcccctgca agtgc 35

<210> SEQ ID NO 29
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 29
ggttgtggga ccaaggctac agcccctgca agtgc 35

<210> SEQ ID NO 30
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 30
ggttgtggga ccaaggatac agcccctgca agtgc 35

<210> SEQ ID NO 31
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 31
ggttgtggga ccaaggacac agcccctgca agtgc 35

<210> SEQ ID NO 32
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 32
ggttgtggga ccaaggatgc agcccctgca agtgc 35

<210> SEQ ID NO 33
<211> LENGTH: 35
<212> TYPE: DNA

-continued

<213> ORGANISM: Artificial Sequence
<220> FEATURE:
<223> OTHER INFORMATION: Synthetic oligonucleotide

<400> SEQUENCE: 33
ggttgtggga ccaaggcgac agcccctgca agtgc 35

<210> SEQ ID NO 34
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 34
ggttgtggga ccaaggaacc agcccctgca agtgc 35

<210> SEQ ID NO 35
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 35
ggttgtggga ccaaggaacc agcccctgca agtgc 35

<210> SEQ ID NO 36
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 36
ggttgtggga ccaaggtacc agcccctgca agtgc 35

<210> SEQ ID NO 37
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 37
ggttgtggga ccaaggggac agcccctgca agtgc 35

<210> SEQ ID NO 38
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 38
tcaggagctc ccccctcgac ccaggataac cctca 35

<210> SEQ ID NO 39
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 39
agatactggg gcccaggact ccgtgctgac ccaaa 35

-continued

<210> SEQ ID NO 40
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 40
tggggcccag cactccatcc tgacccaaaa tcctg 35

<210> SEQ ID NO 41
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 41
tgcctgggtc caagggatta ctggaggaaa gcggt 35

- 14 -